United States Patent
Nishiyama et al.

(10) Patent No.: US 9,598,399 B2
(45) Date of Patent: Mar. 21, 2017

(54) COMPOUND SUITABLE FOR DETECTION OF MITOCHONDRIAL COMPLEX-1

(71) Applicant: HAMAMATSU PHOTONICS K.K., Hamamatsu-shi, Shizuoka (JP)

(72) Inventors: Shingo Nishiyama, Hamamatsu (JP); Norihiro Harada, Hamamatsu (JP); Hideo Tsukada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/422,834

(22) PCT Filed: Aug. 22, 2013

(86) PCT No.: PCT/JP2013/072442
§ 371 (c)(1),
(2) Date: Feb. 20, 2015

(87) PCT Pub. No.: WO2014/030709
PCT Pub. Date: Feb. 27, 2014

(65) Prior Publication Data
US 2015/0225368 A1 Aug. 13, 2015

(30) Foreign Application Priority Data

Aug. 24, 2012 (JP) .................................. 2012-185650

(51) Int. Cl.
*C07D 401/12* (2006.01)
*A61K 51/04* (2006.01)

(52) U.S. Cl.
CPC ........ *C07D 401/12* (2013.01); *A61K 51/0459* (2013.01)

(58) Field of Classification Search
None
See application file for complete search history.

(56) References Cited

U.S. PATENT DOCUMENTS 4,837,217 A * 6/1989 Ogura et al. ............. 514/252.01

FOREIGN PATENT DOCUMENTS

| | | |
|---|---|---|
| CN | 86102700 A | 12/1986 |
| CN | 102014969 A | 4/2011 |
| CN | 102336741 A | 2/2012 |
| EP | 0199281 | 10/1986 |
| EP | 0665223 A1 | 8/1995 |
| JP | S61-243078 A | 10/1986 |
| JP | S62-207262 A | 9/1987 |
| JP | S63-159373 A | 7/1988 |
| JP | H07-252236 A | 10/1995 |
| JP | 2006-199615 A | 8/2006 |
| JP | 2011-513306 A | 4/2011 |
| WO | WO 2005/079391 | 9/2005 |
| WO | WO 2008/023780 A1 | 2/2008 |
| WO | WO 2014/026079 | * 2/2014 |

OTHER PUBLICATIONS

English-language translation of International Preliminary Report on Patentability (IPRP) dated Mar. 5, 2015 that issued in WO Patent Application No. PCT/JP2013/072442.

Marc C. Huisman, et al., "Initial Characterization of an [18]F-Labeled Myocardial Perfusion Tracer," The Journal of Nuclear Medicine, vol. 49, No. 4, 2008, pp. 630-636.

Padmaja Yalamanchili, et al., "Mechanism of uptake and retention of F-18 BMS-747158-02 in cardiomyocytes: A novel PET myocardial imaging agent," Journal of Nuclear Cardiology, vol. 14, No. 6, 2007, pp. 782-788.

Harada et al., "Development of novel PET probes, [$^{18}$F]BCPP-EF, [$^{18}$F]BCPP-BF, and [$^{11}$C]BCPP-EM for mitochondrial complex 1 imaging in the living brain", Journal of Labelled Compounds and Radiopharmaceuticals, vol. 56, No. 11, Jul. 30, 2013, pp. 553-561, XP055240716.

* cited by examiner

*Primary Examiner* — Emily Bernhardt
(74) *Attorney, Agent, or Firm* — Drinker Biddle & Reath LLP

(57) ABSTRACT

Provided is a compound represented by formula (1-0):

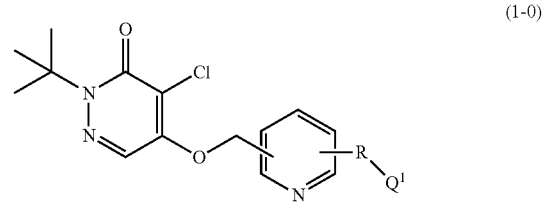

wherein in formula (1-0), R represents $-O(CH_2)_n-$, $-O(CH_2)_nOC_2H_4-$, $-CH_2O(CH_2)_n-$ or $-CH_2O(CH_2)_nOC_2H_4-$; n represents an integer from 1 to 5; and $Q^1$ represents F or $-OCH_3$.

3 Claims, 11 Drawing Sheets

[18F]BMS

[18F]BCPP-EF

COMPOUND SUITABLE FOR DETECTION OF MITOCHONDRIAL COMPLEX-1

TECHNICAL FIELD

The present invention relates to a compound suitable for the detection of mitochondrial Complex-1.

BACKGROUND ART

Special attention has been paid to the positive electron (positron) emission tomographic method (PET method) in recent years because this method exhibits superior sensitivity, resolution and quantifiability compared with the single photon emission computed tomographic method (SPECT method).

Diagnoses of various neuropsychiatric disorders including dementia are currently carried out by an evaluation of the glucose metabolism of neurons according to the PET method. At this time, $^{18}$F-fluorodeoxyglucose ([$^{18}$F]FDG) is used as a probe for PET.

CITATION LIST

Patent Literature

Patent Literature 1: Japanese Translation of PCT Application No. 2011-513306

Non Patent Literature

Non-Patent Literature 1: Yalamanchili, P. et al., J. Nucl. Cardiol 14 (2007) 782-788; Huisman et al., J. Nucl. Med, 49:630-636.

SUMMARY OF INVENTION

Technical Problem

However, it has been found that when a cerebral infarction model rat is evaluated according to the PET method using [$^{18}$F]FDG, in a site of ischemic injury of the brain where accumulation of [$^{18}$F]FDG is anticipated to decrease due to the onset of cerebral infarction, accumulation of [$^{18}$F]FDG is increased on the contrary to the anticipation. This implies that [$^{18}$F]FDG is not suitable as a PET probe for an evaluation after a neurological disorder. When microglial cells that are in charge of immunity in the brain are activated, the activated microglial cells accumulate in a site of ischemic injury where an inflammatory reaction has been induced. It has been confirmed that since these accumulated microglial cells take in [$^{18}$F]FDG, abnormal accumulation of [$^{18}$F]FDG in the site of ischemic injury in the brain is increased.

On the other hand, it has been reported that [$^{18}$F]BMS-747158-02 (2-tert-butyl-4-chloro-5-[4-(2-fluoroethoxymethyl)-benzyloxy]-2H-pyridazin-3-one, [$^{18}$F]BMS) serves as a PET probe that recognizes mitochondrial Complex-1 (hereinafter, may be referred to as "MC-1"), and this compound is used in a functional evaluation of the brain or the heart (Patent Literature 1 and Non-Patent Literature 1). In an in vitro evaluation according to an autoradiographic method using rat brain slices, and in an in vivo evaluation according to the PET method using the brain of a living rat, it can be seen that since [$^{18}$F]BMS is relatively highly oil-soluble (log P=1.42), [$^{18}$F]BMS has high permeability through the blood-brain barrier and satisfactory intracerebral migration properties. It has been found that due to its high oil-solubility, [$^{18}$F]BMS has high non-specific binding capacity, and an inhibitory effect cannot be sufficiently checked by an inhibition experiment using rotenone, which is an inhibitory drug specific to the Complex-1.

The present invention was achieved in view of such circumstances, and it is an object of the present invention to provide a compound suitable for the detection of mitochondrial Complex-1, which can also be utilized as a labeling compound for the PET method.

Solution to Problem

The present invention provides a compound represented by formula (1-0):

[Chem. 1]

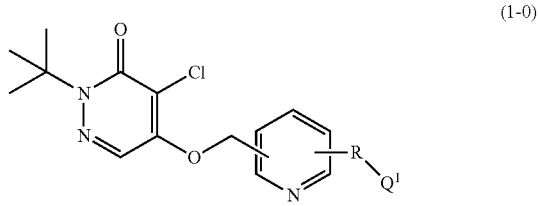

(1-0)

wherein in formula (1-0), R represents —O(CH$_2$)$_n$—, —O(CH$_2$)$_n$OC$_2$H$_4$—, —CH$_2$O(CH$_2$)$_n$— or —CH$_2$O(CH$_2$)$_n$OC$_2$H$_4$—; n represents an integer from 1 to 5; and Q$^1$ represents F or —OCH$_3$.

The compound represented by formula (1-0) is a compound suitable for the detection of mitochondrial Complex-1.

In regard to the compound (1-0), Q$^1$ may be $^{18}$F or —O$^{11}$CH$_3$. In this way, the compound is enabled to emit positrons. Positrons emitted from the compound immediately combine with electrons and emit γ-radiation (annihilation radiation). When this γ-radiation is measured with an apparatus used in the PET method, biodistribution of the above-described compound can be quantitatively imaged over time. That is, the compound can also be utilized as a labeling compound for the PET method.

The present invention provides a compound represented by formula (2-0):

[Chem. 2]

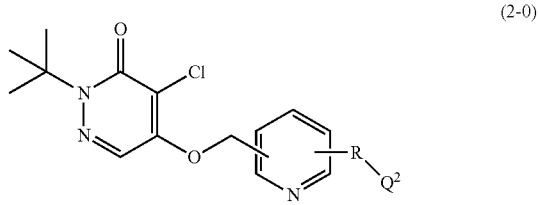

(2-0)

wherein in formula (2-0), R represents —O(CH$_2$)$_n$—, —O(CH$_2$)$_n$OC$_2$H$_4$—, —CH$_2$O(CH$_2$)$_n$— or —CH$_2$O(CH$_2$)$_n$OC$_2$H$_4$—; n represents an integer from 1 to 5; and Q$^2$ represents a detachable substituent (a substituted sulfonyloxy group, a halogen atom, a hydroxyl group, or the like).

When the compound represented by formula (2-0) is used, a compound represented by formula (1-0) can be synthesized efficiently.

Advantageous Effects of Invention

According to the present invention, a compound suitable for the detection of mitochondrial Complex-1, which can also be utilized as a labeling compound for the PET method, can be provided.

DESCRIPTION OF EMBODIMENTS

Figure 1:
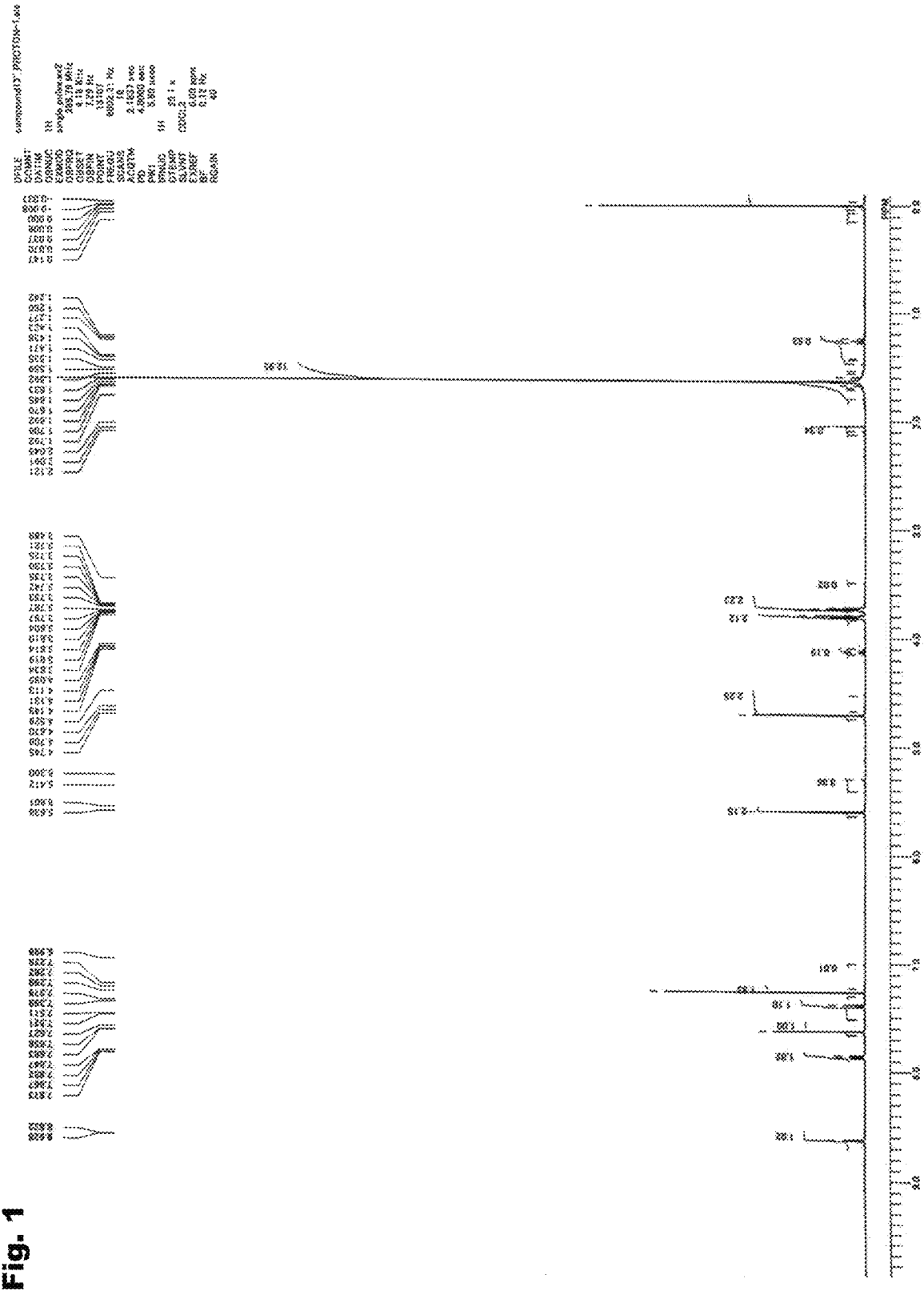
FIG. 1 is the NMR spectral chart for an intermediate of BMS-P.

Hereinafter, suitable embodiments of the present invention are described in detail. However, the present invention is not intended to be limited to the following embodiments.

The compound suitable for the detection of mitochondrial Complex-1 according to the present embodiment is a compound represented by formula (1-0) (hereinafter, may be referred to as "compound (1-0)").

[Chem. 3]

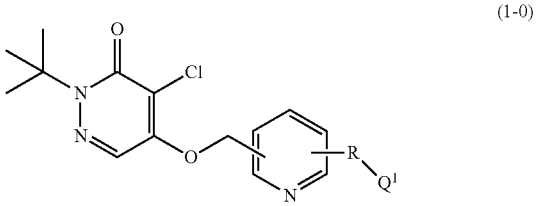

(1-0)

R represents —O(CH$_2$)$_n$—, —O(CH$_2$)$_n$OC$_2$H$_4$—, —CH$_2$O(CH$_2$)$_n$— or —CH$_2$O(CH$_2$)$_n$OC$_2$H$_4$—. n represents an integer from 1 to 5, and is preferably 2 to 4. Q$^1$ represents F or —OCH$_3$, and is preferably $^{18}$F or —O$^{11}$CH$_3$. When —O$^{11}$CH$_3$ or $^{18}$F is used for Q$^1$, the compound (1-0) is enabled to emit positrons. When Q$^1$ is —O$^{11}$CH$_3$, since the half life is as short as 20 minutes, it is also possible to carry out several measurements in one day. When Q$^1$ is $^{18}$F, since the half life is 110 minutes, which is longer than that of —O$^{11}$CH$_3$, it is possible to lengthen one measurement time.

In the pyridine ring, the bonding position of —OCH$_2$— bonded to the pyridazine ring and the bonding position of R are not particularly limited; however, it is preferable that the bonding position of —OCH$_2$— bonded to the pyridazine ring be the 5-position of the pyridine ring, and the bonding position of R is the 2-position of the pyridine ring. The structural formula in which the bonding position of —OCH$_2$— bonded to the pyridazine ring is the 5-position of the pyridine ring, and the bonding position of R is the 2-position of the pyridine ring, is shown below as formula (1-0'):

[Chem. 4]

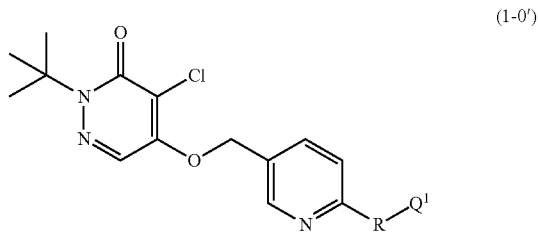

(1-0')

From the viewpoint of binding specificity to mitochondrial Complex-1, the compound suitable for the detection of mitochondrial Complex-1 is preferably a compound represented by formula (1) (hereinafter, may be referred to as "compound (1)"). The compound (1) has lower oil-solubility compared with [$^{18}$F]BMS. Therefore, non-specific binding of the compound (1) is suppressed, and the binding specificity to mitochondrial Complex-1 tends to be higher compared with [$^{18}$F]BMS.

[Chem. 5]

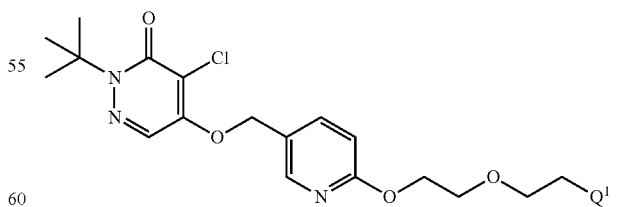

(1)

From the viewpoint of binding affinity to mitochondrial Complex-1, the compound suitable for the detection of mitochondrial Complex-1 is preferably a compound represented by formula (1-2) (hereinafter, may be referred to as "compound (1-2)".

[Chem. 6]

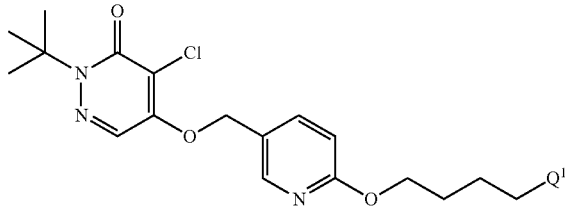

(1-2)

A compound represented by formula (2-0) (hereinafter, may be referred to as "compound (2-0)") is a precursor of the compound (1-0).

[Chem. 7]

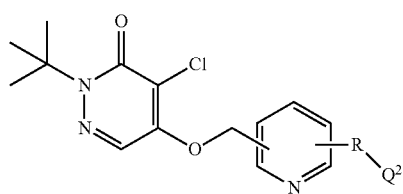

(2-0)

$Q^2$ represents a detachable substituent (a substituted sulfonyloxy group, a halogen atom, a hydroxyl group, or the like).

Examples of the substituted sulfonyloxy group include a tosyloxy group (—OTs), a methanesulfonyloxy group (—OMs), a trifluoromethanesulfonyloxy group (—OTf), and a nitrobenzenesulfonyloxy group (—ONs), and —OTs is preferably used.

Examples of the halogen atom include fluorine, chlorine, bromine, and iodine.

A compound represented by formula (2-0') (hereinafter, may be referred to as compound (2-0')) is a precursor of the compound (1-0').

[Chem. 8]

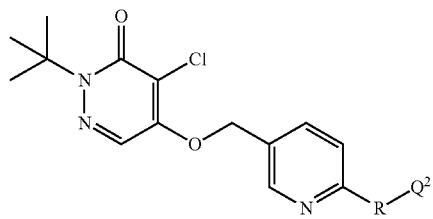

(2-0')

A compound represented by formula (2) (hereinafter, may be referred to as compound (2)) is a precursor of the compound (1).

[Chem. 9]

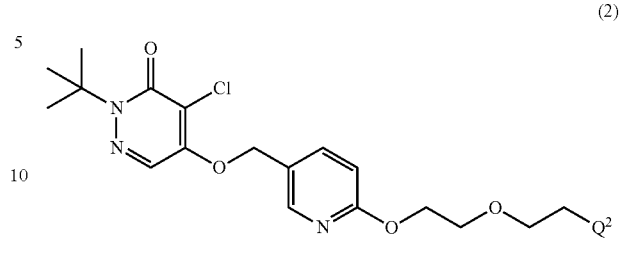

(2)

A compound represented by formula (2-2) is a precursor of the compound (1-2).

[Chem. 10]

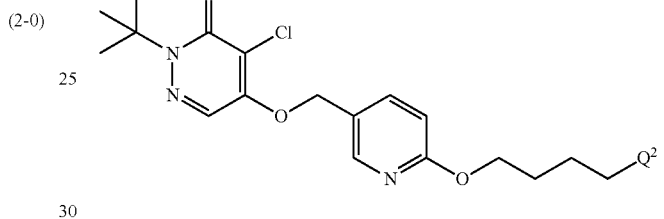

(2-2)

(Method for Synthesizing Precursor)

A compound (2-0) in which R represents —CH$_2$O(CH$_2$)$_n$—; n represents 2; and $Q^2$ represents a hydroxyl group can be synthesized from a known compound. For example, the compound can be synthesized through the synthesis scheme (steps 1 to 10) described in Experiment 2 of the Examples that are described below. A compound (2-0) in which R represents —CH$_2$O(CH$_2$)$_n$OC$_2$H$_4$—; and $Q^2$ represents a hydroxyl group can be synthesized by referring to the synthesis scheme (steps 1 to 10) described in Experiment 2 of the Examples described below, and the synthesis scheme (c) that are described below.

A compound (2) in which $Q^2$ represents a hydroxyl group can be synthesized from a known compound. For example, the compound can be synthesized through the synthesis scheme (a) to (h) described in Experiment 1 of the Examples described below.

A compound (2) in which $Q^2$ represents a tosyloxy group can be synthesized from a known compound. For example, the compound can be synthesized from the compound (2) in which $Q^2$ represents a hydroxyl group, through the synthesis scheme (i) described in the Examples described below.

The method for producing a compound (1) in which $Q^1$ represents F from a compound (2) is carried out by a method of fluorinating the compound (2). For example, when $Q^2$ represents —OTs, the method for fluorinating the compound (2) is represented by the following synthesis scheme (A). Even when $Q^2$ represents another substituted sulfonyloxy group or another halogen atom, a corresponding compound (1) can be synthesized by a similar synthesis scheme.

[Chem. 11]

(A)

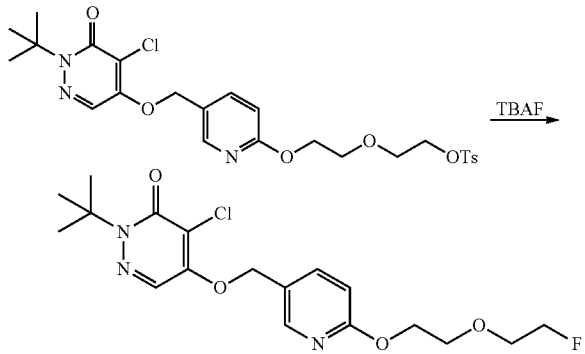

The method for producing a compound (1) in which Q¹ represents $^{18}$F from a compound (2) is carried out by a method of subjecting the compound (2) to [$^{18}$F]fluorination. For example, when Q² represents —OTs, the method of subjecting the compound (2) to [$^{18}$F]fluorination is represented by the following synthesis scheme (B). Even when Q² represents another substituted sulfonyloxy group or another halogen atom, a corresponding compound (1) can be synthesized by a similar synthesis scheme.

[Chem. 12]

(B)

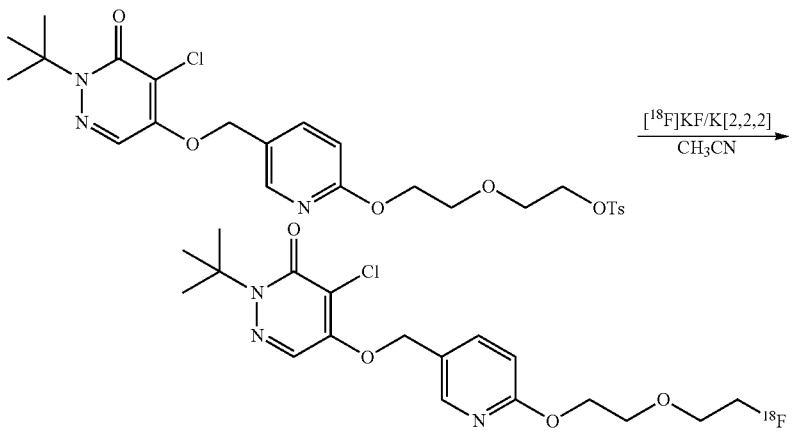

Regarding the method of subjecting the compound (2) to [$^{18}$F]fluorination, the compound (2) can be [$^{18}$F]fluorinated by allowing the compound (2) to react with a complex of a macrocyclic ligand and [$^{18}$F]KF in a solvent.

The solvent used for the [$^{18}$F]fluorination is not particularly limited as long as it can dissolve the starting material to some extent. Examples thereof include acetonitrile, dimethylformamide (DMF), and dimethyl sulfoxide (DMSO), and acetonitrile is preferably used.

Examples of the macrocyclic ligand include 4,7,13,16,21,24-hexaoxa-1,10-diazabicyclo[8.8.8]hexacosane (K[2.2.2]) and 1,4,7,10,13,16-hexaoxacyclooctadecane (18-crown-6), and K[2.2.2] is preferably used.

The method for producing a compound (1) in which Q¹ represents —OCH₃, from a compound (2) in which Q² represents a hydroxyl group, is represented by, for example, the following synthesis scheme (C):

[Chem. 13]

(C)

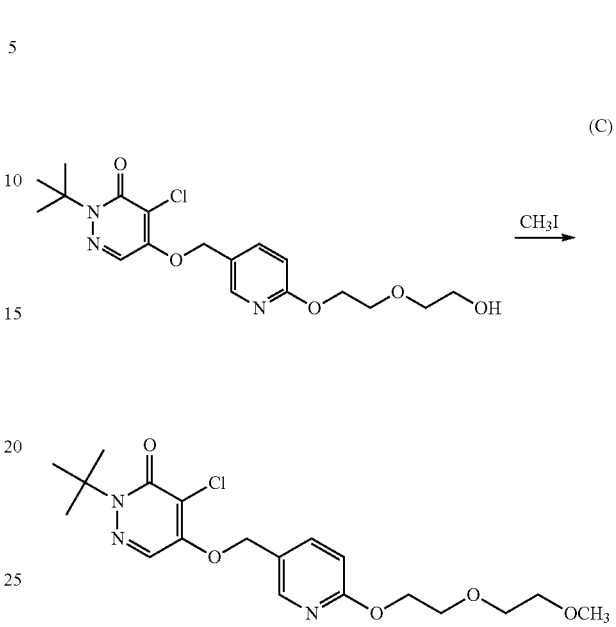

The method for producing a compound (1) in which Q¹ represents —O$^{11}$CH₃, from a compound (2) in which Q² represents a hydroxyl group, is represented by, for example, the following synthesis scheme (D):

[Chem. 14]

(D)

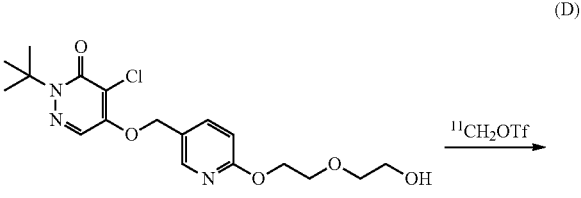

-continued

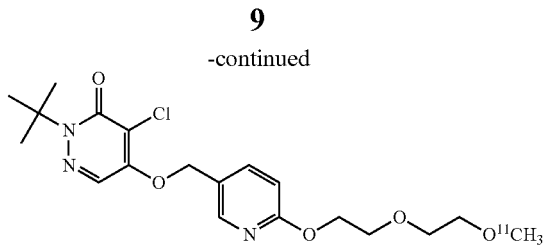

In the above synthesis scheme (D), $^{11}CH_3OTf$ can be synthesized by a known method. For example, $^{11}CH_3OTf$ can be synthesized by reaction formula (E):

[Chem. 15]

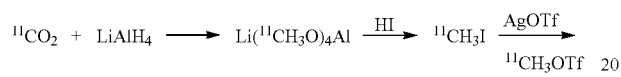
(E)

Compound (1) tends to specifically bind to mitochondrial Complex-1 when administered to a living body. Compound (1-2) tends to bind to mitochondrial Complex-1 with high affinity when administered to a living body. Therefore, compound (1-0) is suitable for the detection of mitochondrial Complex-1. For example, when a fluorescent dye or the like is bound to the compound (1-0), or the compound (1-0) is subjected to positron labeling, the compound (1-0) can be used as a labeling compound for mitochondrial Complex-1. Particularly, in a case in which $Q^1$ of the compound (1-0) is —$O^{11}CH_3$ or $^{18}F$, the compound (1-0) is enabled to emit positrons. The positrons emitted from the compound (1-0) immediately combine with electrons and emit γ-radiation. When this γ-radiation is measured with an apparatus used in the PET method, the biodistribution of the compound (1-0) can be imaged quantitatively over time. Therefore, when the compound (1-0) is used, a site where mitochondrial Complex-1 exists in the body of a test subject is detected, and changes thereof can be visualized over time.

The compound (1-0) is useful as a reagent for the detection of mitochondrial Complex-1. This detection reagent includes the compound (1-0), and when the reagent is administered to a living body, the site where mitochondrial Complex-1 exists can be efficiently detected by measuring the γ-radiation emitted from the compound (1-0) in the body by the PET method. The detection reagent is especially suitable for the detection of mitochondrial Complex-1 in the brain.

The compound (1-0) is also useful as a diagnostic drug for Parkinson's disease. When this diagnostic drug is used, diagnosis of Parkinson's disease is enabled by efficiently detecting the site where mitochondrial Complex-1 exists in the body.

The reagent for the detection of mitochondrial Complex-1 and the diagnostic drug for Parkinson's disease can be produced by, for example, dissolving the compound (1-0) in an arbitrary buffer solution. In this case, the detection reagent and the diagnostic drug are provided as solutions, and the solutions may contain other components such as a surfactant, an antiseptic agent and a stabilizer, in addition to the buffering components. The method for administration is usually intravenous administration.

Examples of the object of the reagent for the detection of mitochondrial Complex-1 and the diagnostic drug for Parkinson's disease include, but are not limited to, human, monkey, mouse, and rat. On the occasion of performing a PET analysis using the compound (1-0) according to the present embodiment, the method for analysis is not particularly limited and can be carried out according to a known method.

EXAMPLES

Hereinafter, the present invention will be described in more detail by way of Examples. However, the present invention is not intended to be limited to these Examples.

In the following Examples, unless particularly stated otherwise, the silica gel used in silica gel column chromatography was SILICA GEL 60N (for flash chromatography) 40 to 50 μm manufactured by Kanto Chemical Co., Inc.).

Experiment 1

Synthesis of BCPP-EF

BCPP-EF was synthesized according to step 1 to step 10 described below. The various steps are described below.

Step 1

Compound 3 was synthesized according to synthesis scheme (a).

[Chem. 16]

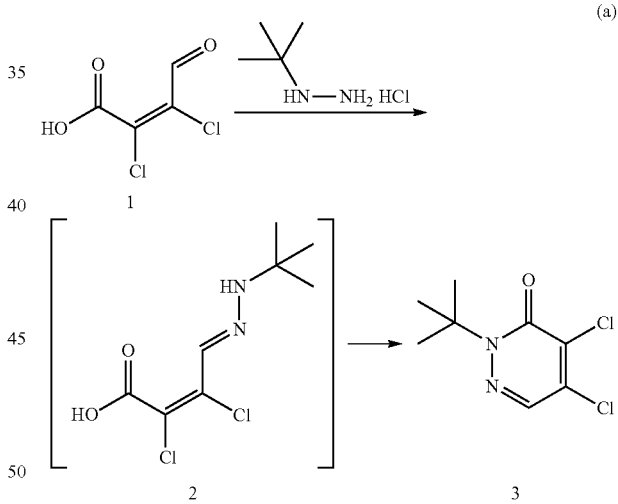

Mucochloric acid 1 (50 g, 0.29 mol) was dissolved in water (440 mL), and sodium carbonate (15.3 g, 0.14 mol) was added thereto. tert-Butylhydrazine hydrochloride (36.9 g, 0.29 mol) was added to that solution at 0° C. The obtained reaction mixture was stirred for 2.5 hours. A precipitated solid was filtered and washed with cold water, and then the precipitated solid was dried under reduced pressure. Thus, intermediate 2 was obtained.

Acetic acid (500 mL) was added to the intermediate 2, and the reaction mixture was heated to reflux for 30 minutes. Acetic acid in the reaction mixture was distilled off under reduced pressure, and then the reaction mixture was partitioned using methylene chloride and an aqueous solution of sodium hydrogen carbonate. The organic layer was washed with water and then dried over anhydrous magnesium sulfate, and the organic layer was concentrated under reduced pressure. The concentrated residue was purified by silica gel chromatography (heptane:chloroform=7:3 to 0:10), and compound 3 (52.9 g, yield 80%) was obtained as a pale yellow solid.

Step 2

Compound 4 was synthesized according to synthesis scheme (b).

[Chem. 17]

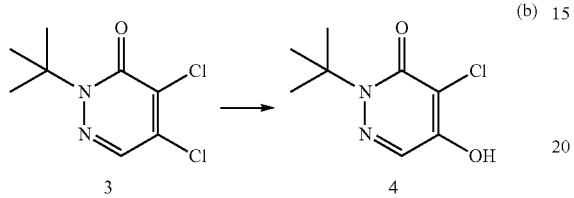

To a 1,4-dioxane solution of the compound 3 (2 g, 9 mmol), an aqueous solution (15 mL) of potassium hydroxide (1.5 g, 27 mmol) was added, and the mixture was heated to reflux for 5 hours. The obtained mixture was poured into ice water, concentrated hydrochloric acid was added thereto, and a solid thus precipitated (crude form) was collected by filtration. The crude form was washed with water and heptane in this order, and thus compound 4 (1.6 g, yield 91%) was obtained.

Step 3

Compound 6 was synthesized according to synthesis scheme (c).

[Chem. 18]

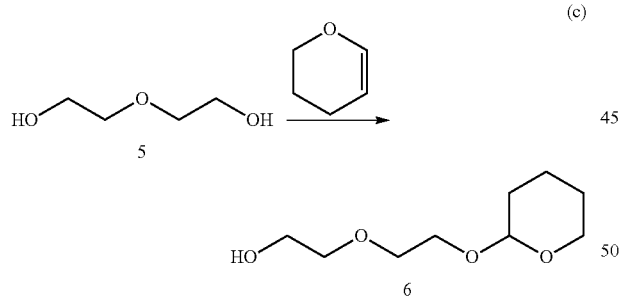

To a mixture of diethylene glycol (22.8 mL, 0.24 mol) and 3,4-dihydro-2H-pyrane (21.7 mL, 0.24 mol) in THF (40 mL) and methylene chloride (400 mL), p-toluenesulfonic acid monohydrate (4.57 g, 24 mmol) was added at −10° C., and the reaction mixture was stirred for one hour. Water was added to the reaction mixture, and the reaction mixture was partitioned with ether. The organic layer was washed with saturated brine and was dried over anhydrous sodium sulfate. Thereafter, the organic layer was concentrated under reduced pressure. The concentrated residue was purified by silica gel chromatography (heptane:ethyl acetate=50:50 to 0:100), and thus compound 6 (14 g, yield 31%) as a colorless liquid was obtained.

Step 4

Compound 9 was synthesized according to synthesis scheme (d).

[Chem. 19]

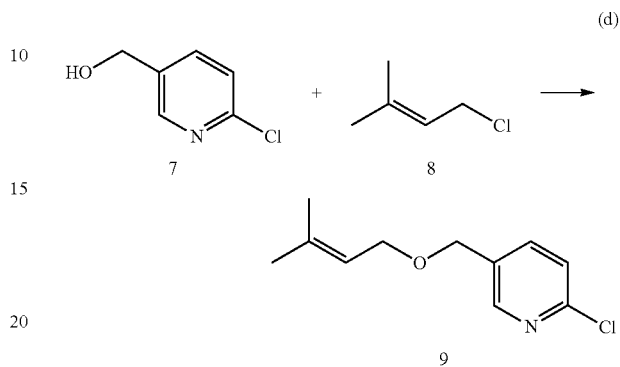

In an argon atmosphere, a DMF solution (30 mL) of 6-chloro-3-pyridinemethanol 7 (5 g, 34.8 mmol) was slowly added to sodium hydride (1.51 g, 37.8 mmol (60% in oil)) at 0° C. Thereafter, 1-chloro-3-methyl-2-butene 8 (4.11 mL, 36.5 mmol) was further added to the reaction mixture, and the reaction mixture was stirred for one hour at 25° C. 1-Chloro-3-methyl-2-butene (2.0 mL, 17.7 mmol) was further added to the remaining raw materials, and the reaction mixture was stirred for one hour at 50° C.

Sodium hydride (1.51 g, 37.8 mmol (60% in oil)) and 1-chloro-3-methyl-2-butene (8.0 mL, 71.1 mmol) were added to the remaining raw materials, and the reaction mixture was stirred for 30 minutes at 50° C. Water was added to the reaction mixture, and the reaction mixture was partitioned with ethyl acetate. The organic layer was washed with saturated brine, and was dried over anhydrous sodium sulfate. Thereafter, the organic layer was concentrated under reduced pressure. The concentrated residue was purified by silica gel chromatography (heptane:ethyl acetate=95:5 to 85:15), and compound 9 (7.0 g, yield 96%) was obtained as a colorless liquid.

Step 5

Compound 10 was synthesized according to synthesis scheme (e).

[Chem. 20]

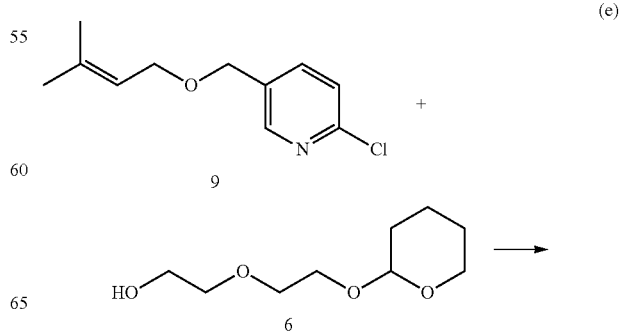

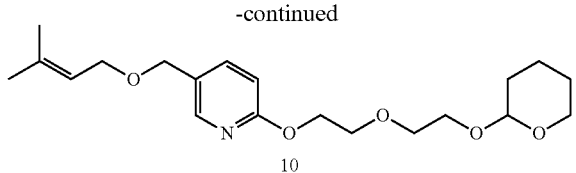

10

In an argon atmosphere, a 1,4-dioxane solution (8 mL) of compound 6 (1.90 g, 10 mmol) was slowly added to sodium hydride (320 mg, 8 mmol (60% in oil)) at 0° C., and the reaction mixture was stirred for 30 minutes at 60° C. Thereafter, a 1,4-dioxane solution (4 mL) of compound 9 (0.84 g, 4 mmol) was added to the reaction mixture, and the reaction mixture was stirred for 30 minutes at 170° C. in a microwave range. After the reaction mixture was cooled, a saturated aqueous solution of ammonium chloride was added to the reaction mixture, and the mixture was partitioned with chloroform. The organic layer was washed with water and saturated brine, and was dried over anhydrous magnesium sulfate. Thereafter, the organic layer was concentrated under reduced pressure. The concentrated residue was purified by silica gel chromatography (heptane:ethyl acetate=95:5 to 85:15), and thus compound 10 (4.9 g, yield 96%) was obtained.

Step 6

Compound 11 was synthesized according to synthesis scheme (f).

[Chem. 21]

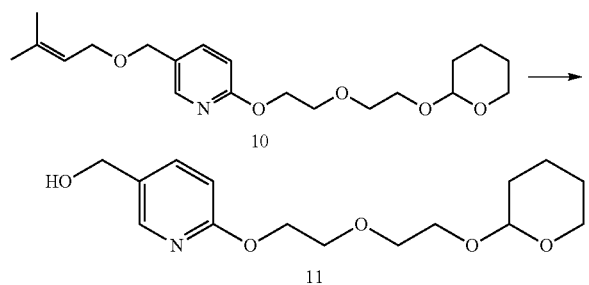

In an argon atmosphere, compound 10 (5 g, 13.6 mmol) was slowly added to a DMSO solution (130 mL) of potassium tert-butoxide (15.3 g, 0.13 mol), and the reaction mixture was stirred for 40 minutes at 60° C. After the reaction mixture was cooled, a saturated aqueous solution of ammonium chloride was added to the reaction mixture, and the mixture was partitioned with ethyl acetate. The organic layer was washed with water and saturated brine, and was dried over anhydrous magnesium sulfate. Thereafter, the organic layer was concentrated under reduced pressure. The concentrated residue was purified by silica gel chromatography (heptane:ethyl acetate=80:20), and thus compound 11 (2.7 g, yield 68%) was obtained as a pale yellow liquid.

Step 7

Compound 12 was synthesized according to synthesis scheme (g).

[Chem. 22]

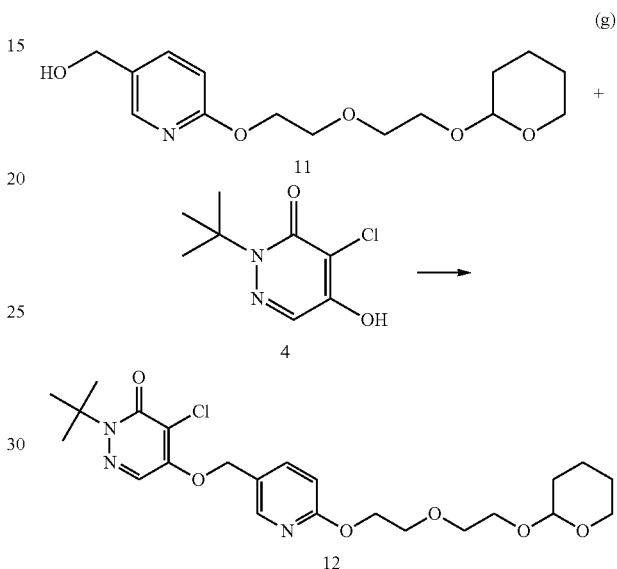

In an argon atmosphere, diisopropyl azodicarboxylate (2.09 mL, 10.6 mmol) was added to a THF solution (100 mL) of compound 4 (1.43 g, 7.04 mmol), compound 11 (2.3 g, 7.74 mmol), and triphenylphosphine (2.77 g, 10.6 mmol), and the reaction mixture was stirred for 16 hours at 25° C. Water was added to the reaction mixture, and the mixture was partitioned with ethyl acetate. The organic layer was washed with saturated brine, and was dried over anhydrous magnesium sulfate. Thereafter, the organic layer was concentrated under reduced pressure. The concentrated residue was purified by silica gel chromatography (first time, heptane:ethyl acetate=90:10 to 60:40, second time, chloroform:methanol=99:1) and thus compound 12 (2.7 g, yield 80%) was obtained.

Step 8

Compound 13 was synthesized according to synthesis scheme (h).

[Chem. 23]

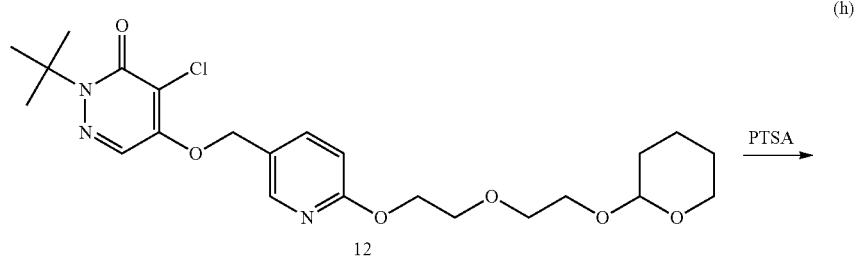

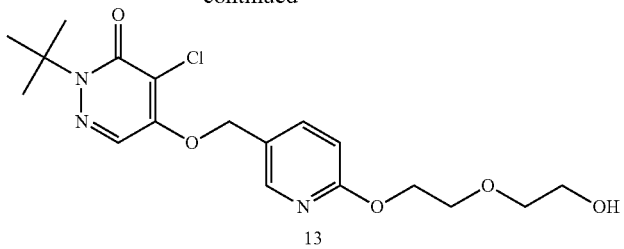

13 p-Toluenesulfonic acid monohydrate (2 mg, 0.01 mmol) was added to a methanol solution (1 mL) of compound 12 (96 mg, 7.2 mmol), and the reaction mixture was stirred for 16 hours at 25° C. The reaction mixture was concentrated under reduced pressure, and then the concentrated residue was purified by silica gel chromatography (heptane:ethyl acetate=70:30 to 20:80), and compound 13 (96.9 mg, yield 99%) was obtained as a colorless solid.

Step 9

Compound 14 was synthesized according to synthesis scheme (i).

[Chem. 24]

(i)

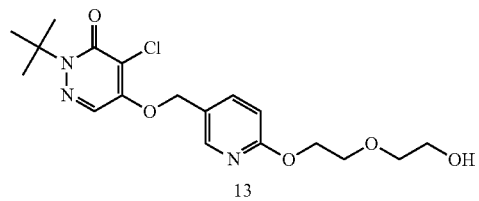

13

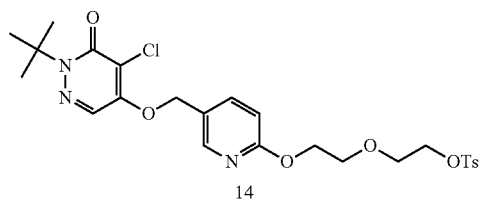

14 p-Toluenesulfonyl chloride (0.32 g, 1.69 mmol) was added to a methylene chloride solution (10 mL) of compound 13 (450 mg, 1.13 mmol), triethylamine (1.58 mL, 11.3 mmol) and 4-dimethylaminopyridine (13.8 mg, 0.11 mmol) at or below −10° C., and the reaction mixture was stirred for 16 hours. Water was added to the reaction mixture, and the target compound was extracted two times with methylene chloride. The organic layer was washed with saturated brine, and was dried over anhydrous magnesium sulfate. Thereafter, the organic layer was concentrated under reduced pressure. The concentrated residue was purified by silica gel chromatography (heptane:ethyl acetate=90:10 to 40:60), and thus compound 14 (610 mg, yield 97%) was obtained.

Step 10

Compound 15 (BCPP-EF) was synthesized according to synthesis scheme (j).

[Chem. 25]

(j)

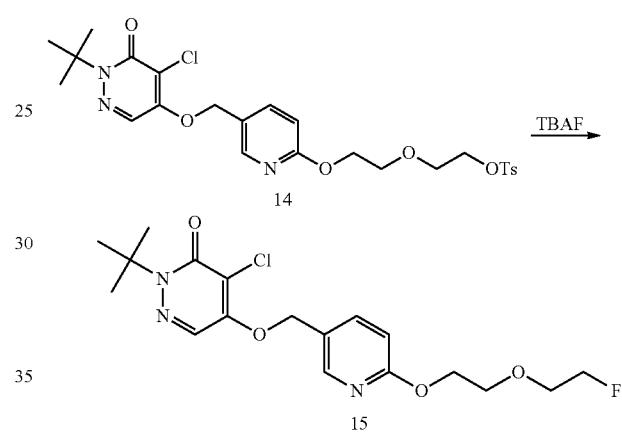

14

15

In an argon atmosphere, a mixture of compound 14 (110 mg, 0.2 mmol) and tetrabutylammonium fluoride (0.6 mL, 0.6 mmol (in THF, 1.0 mol/L) was stirred for 16 hours at 25° C. The reaction mixture was concentrated under reduced pressure, and then the concentrated residue was purified by silica gel chromatography (heptane:ethyl acetate=90:10 to 50:50), and thus compound 15 (70 mg, yield 88%), which was BCPP-EF, was obtained.

Synthesis of BCPP-EM

BCPP-EM was synthesized according to the step 1 to step 8 described above and the step 11 described below. Hereinafter, step 11 is explained.

Step 11

Compound 16 was synthesized according to synthesis scheme (k).

[Chem. 26]

(k)

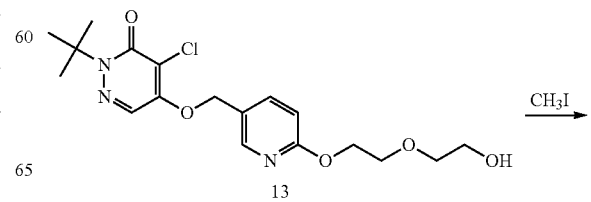

13

-continued

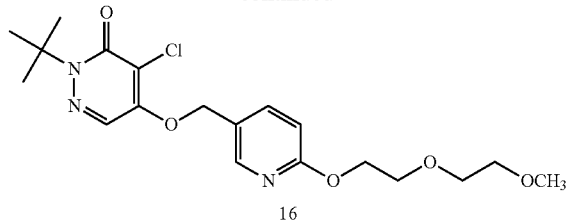

16

In an argon atmosphere, a 1,4-dioxane solution (2 mL) of compound 13 (80 mg, 0.2 mmol) was added to sodium hydride (12 mg, 0.3 mmol (60% in oil)) at 0° C. Thereafter, methyl iodide (125 μL, 2 mmol) was added to the reaction mixture, the reaction mixture was stirred for one hour at 25° C. in a sealed tube container. After the reaction mixture was cooled, water was added to the reaction mixture, and the mixture was partitioned with ethyl acetate. The organic layer was washed with saturated brine, and was dried over anhydrous magnesium sulfate. Thereafter, the organic layer was concentrated under reduced pressure. The concentrated residue was purified by silica gel chromatography (heptane: ethyl acetate=70:30 to 30:70), and thus compound 16 (62 mg, yield 75%) was obtained.

Synthesis of [$^{18}$F]BCPP-EF

[$^{18}$F]BCPP-EF (compound 17) was synthesized according to the step 1 to step 9 described above and the synthesis scheme (1) described below.

was produced. A CH$_3$CN (Sigma-Aldrich Co., St. Louis, USA) solution (1.5 mL) of a precursor (compound 14, 6.29 mg, 11.3 μmol) was added to [$^{18}$F]KF/K[2,2,2], and the mixture was fluorinated for 10 minutes at 80° C. To the obtained reaction mixture, a mixture of CH$_3$CN and H$_2$O (CH$_3$CN:H$_2$O=3:7, 1.5 mL) was added, and thereby the reaction was terminated. Subsequently, the reaction mixture was transferred to a HPLC injector. The reaction vessel was washed together with a mixture of CH$_3$CN and H$_2$O (CH$_3$CN:H$_2$O 3:7, 1.5 mL), and the mixture was similarly transferred to the HPLC injector. A crude product was purified by HPLC [column: INERTSIL ODS-3 (5μ, 10.0× 250 mm, GL Sciences, Inc., Tokyo), mobile phase: CH$_3$CN: H$_2$O=500:500, flow rate: 6 mL/min, wavelength: 254 nm]. A radioactive peak obtained at a retention time of 17.4 minutes was fractionated, and the fractionated solution was concentrated and dried to solid in an evaporator. Subsequently, the concentrated and dried product was redissolved in 0.1% Tween 80/physiological saline (5 mL), and thus [$^{18}$F]BCPP-EF (2.36 GBq) was collected.

A portion of the product was taken and analyzed by HPLC [column: FINEPAK SIL C18S (5μ, 4.6×150 mm, JASCO Corp., Tokyo), mobile phase: CH$_3$CN:30 mM CH$_3$ONH$_4$: CH$_3$COOH=500:500:2, flow rate: 2 mL/min, wavelength: 254 nm]. The radiochemical yield, specific radioactivity, and radiochemical purity were 16.98% (decay corrected), 84.3 GBq/μmol, and 100%, respectively. The total synthesis time was approximately 63 minutes from the end of bombardment (BOB).

[Chem. 27]

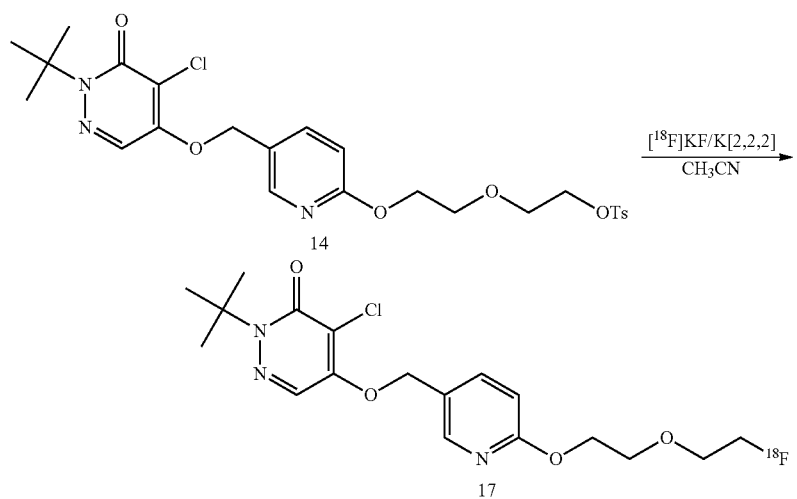

(1)

Label synthesis was carried out using [$^{18}$F] labeling compound automatic synthesis apparatuses (F-110, F-120, Sumitomo Heavy Industries, Ltd., Tokyo). [$^{18}$F]F$^-$ that was collected from the target and trapped by an anion exchange resin, AG1-X8 (Bio-Rad Laboratories, Inc., Hercules, USA) was desorbed with a 40 mM aqueous K$_2$CO$_3$ solution (0.5 mL, 20 μmol). To the obtained solution, a CH$_3$CN (Sigma-Aldrich Co., St. Louis, Mo., USA) solution (2 mL) of K[2,2,2] (Merck KGaA, Darmstadt, Germany) (15 mg, 20 μmol) was added, and the reaction mixture was azeotropically dehydrated under a stream of He gas. CH$_3$CN (1 mL) was added to the residue, azeotropic dehydration was repeated two times, and thus dehydrated [$^{18}$F]KF/K[2,2,2]

In regard to [$^{18}$F]BCPP-EF, when the compound was synthesized with 3.54 mg of the precursor (compound 14), the radiochemical yield was 4.02%. When the amount of the precursor was increased to 6.29 mg, the radiochemical yield was increased to 16.98%. The radiochemical purity of the obtained final product was 100%, the specific radioactivity was 84.3 GBq/μmol. Purity and yield sufficient for a PET experiment could be obtained.

Synthesis of [$^{11}$C]BCPP-EM

[$^{11}$C]BCPP-EM was synthesized according to the step 1 to step 8 described above and the synthesis scheme (m) described below.

[Chem. 28]

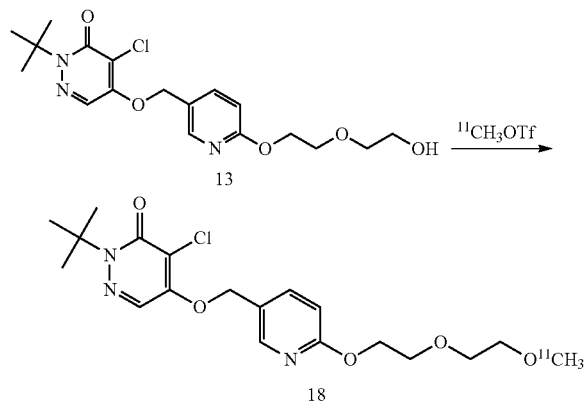

Protons were accelerated to 18 MeV using a cyclotron (HM-18, Sumitomo Heavy Industries, Ltd., Tokyo). On the other hand, a target gas was provided by encapsulating pure nitrogen gas (G grade, Japan Fine Products Corp., Kanagawa) at a pressure of approximately 17 kg/cm$^2$. The target gas was irradiated with the protons at a current value of approximately 20 μA, and [$^{11}$C] was produced by a $^{14}$N(p, α)$^{11}$C nuclear reaction. [$^{11}$C] existed in the chemical form of [$^{11}$C]CO$_2$ in the target gas. The target gas containing [$^{11}$C]CO$_2$ was introduced into a cooled 0.1 M LiAlH$_4$/tetrahydrofuran (THF) solution (500 μL) (ABX Advanced Biochemical Compounds GmbH, Germany) in an automatic synthesis apparatus (Sumitomo Heavy Industries, Ltd., Tokyo). The flow rate of the target gas at this time was 400 mL/min. After the target gas was introduced, the obtained reaction mixture was bubbled with nitrogen gas (gas flow rate, 200 mL/min), and THF was distilled off by heating the reaction mixture to 200° C. After THF was distilled off, the reactor was first cooled, hydroiodic acid (Nacalai Tesque, Inc., Kyoto, 0.5 mL) was added to the reaction mixture, and the mixture was heated to 150° C. Produced [$^{11}$C]methyl iodide was distilled and passed through an AgOTf (Sigma-Aldrich Co., USA) column that had been heated to 200° C., and thereby [$^{11}$C]methyl triflate was obtained. [$^{11}$C]methyl triflate that passed through the column was immediately introduced into a solution of the precursor (compound 13).

The precursor (compound 13, 2 mg) was dissolved in 2-butanone (Wako Pure Chemical Industries, Ltd., Tokyo, 0.3 mL). NaH (about 2 mg) was added to the obtained precursor solution, and the mixture was mixed. To the obtained precursor solution, the [$^{11}$C]methyl triflate that had been distilled was introduced, and at the time point where radioactivity reached an equilibrium, introduction of the [$^{11}$C]methyl triflate was terminated. Thereafter, a methylation reaction of the precursor was carried out under the conditions of 40° C. for 5 minutes.

A solution of [$^{11}$C]BCPP-EM was fractionated by high performance liquid chromatography (static phase: MEGA-PAK SIL C18-10 7.6×250 mm (JASCO Corp., Tokyo), mobile phase: acetonitrile (Wako Pure Chemical Industries, Ltd., Osaka):30 mM aqueous solution of ammonium acetate (Wako Pure Chemical Industries, Ltd., Osaka)=450:550, flow rate: 6 mL/min, wavelength: 254 nm). The eluent was distilled off from the fractionated solution in an evaporator (Sumitomo Heavy Industries, Ltd., Tokyo), physiological saline (Otsuka Pharmaceutical Co., Ltd., Tokyo) was added to the residue, and this was taken as a final preparation.

Radioactivity of the final preparation was measured (Hitachi Aloka Medical, Ltd., Tokyo). A portion of the final preparation was analyzed by high performance liquid chromatography (static phase: FINEPACK C18-S 4.6×150 mm (JASCO Corp., Tokyo), mobile phase: acetonitrile (Wako Pure Chemical Industries, Ltd., Osaka): 30 mM ammonium acetate (Nacalai Tesque Inc., Kyoto): acetic acid (Wako Pure Chemical Industries, Ltd., Osaka)=500:500:2, flow rate: 2 mL/min, wavelength: 254 nm).

When the target gas was irradiated with the protons for approximately 60 minutes, the production amount of [$^{11}$C]BCPP-EM was 0.26 to 2.01 GBq, and the radiochemical purity was 93.6% or more.

In separation HPLC, the retention time of the precursor of [$^{11}$C]BCPP-EM (compound 13) was 5.2 minutes, and the retention time of [$^{11}$C]BCPP-EM was 10 minutes. The retention time of [$^{11}$C]BCPP-EM in analytic HPLC was 4.0 minutes.

Experiment 2

Synthesis of BMS-P

BMS-P (compound 15") was synthesized according to the step 1 to step 12 described below. Hereinafter, the various steps are explained.

[Chem. 29]

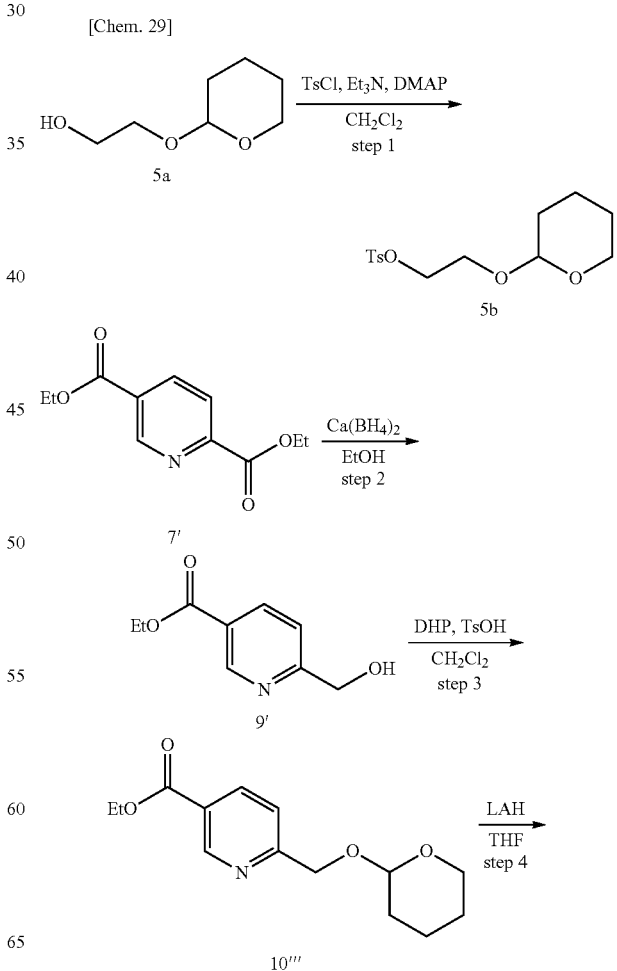

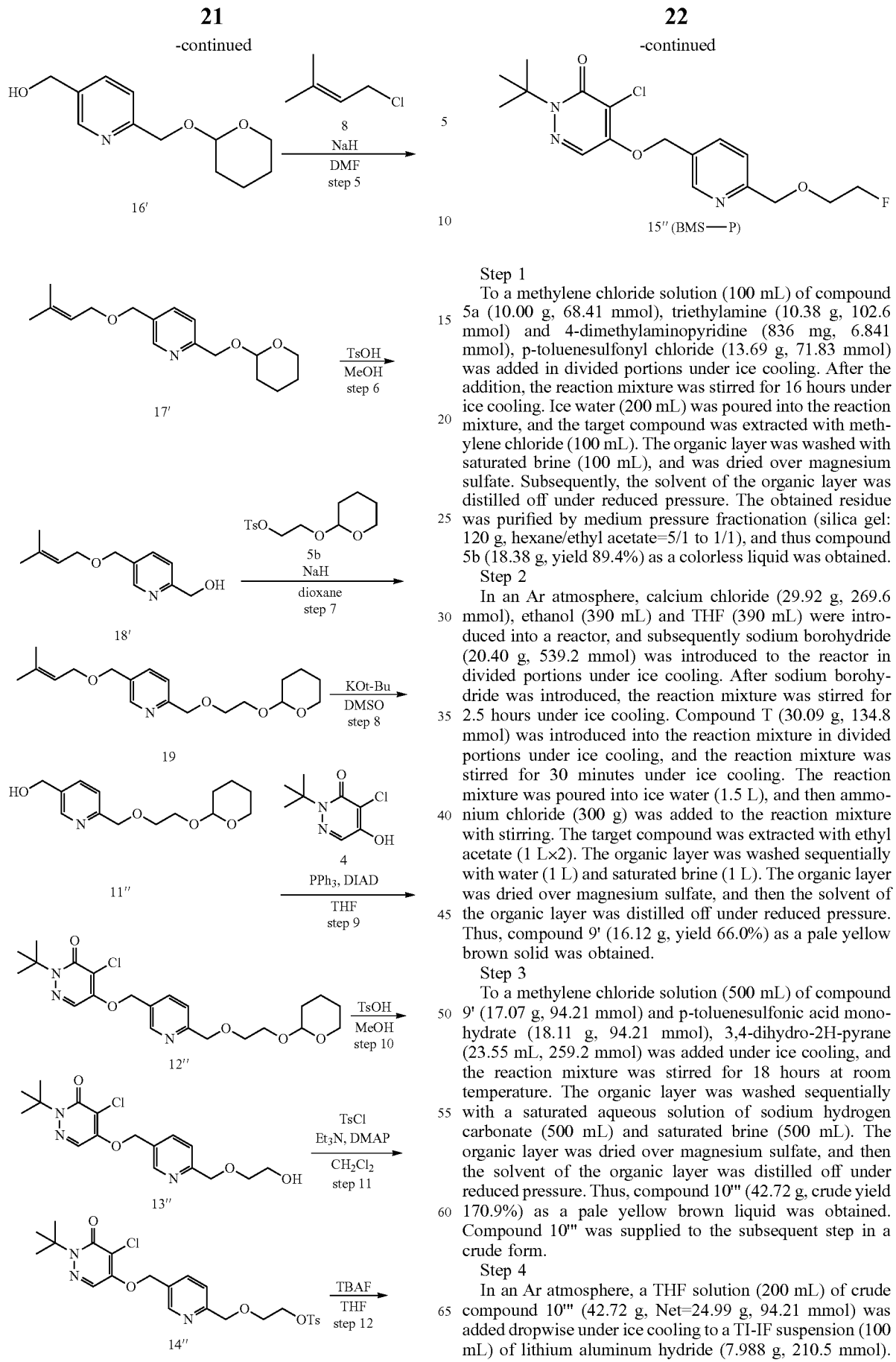

Step 1

To a methylene chloride solution (100 mL) of compound 5a (10.00 g, 68.41 mmol), triethylamine (10.38 g, 102.6 mmol) and 4-dimethylaminopyridine (836 mg, 6.841 mmol), p-toluenesulfonyl chloride (13.69 g, 71.83 mmol) was added in divided portions under ice cooling. After the addition, the reaction mixture was stirred for 16 hours under ice cooling. Ice water (200 mL) was poured into the reaction mixture, and the target compound was extracted with methylene chloride (100 mL). The organic layer was washed with saturated brine (100 mL), and was dried over magnesium sulfate. Subsequently, the solvent of the organic layer was distilled off under reduced pressure. The obtained residue was purified by medium pressure fractionation (silica gel: 120 g, hexane/ethyl acetate=5/1 to 1/1), and thus compound 5b (18.38 g, yield 89.4%) as a colorless liquid was obtained.

Step 2

In an Ar atmosphere, calcium chloride (29.92 g, 269.6 mmol), ethanol (390 mL) and THF (390 mL) were introduced into a reactor, and subsequently sodium borohydride (20.40 g, 539.2 mmol) was introduced to the reactor in divided portions under ice cooling. After sodium borohydride was introduced, the reaction mixture was stirred for 2.5 hours under ice cooling. Compound T (30.09 g, 134.8 mmol) was introduced into the reaction mixture in divided portions under ice cooling, and the reaction mixture was stirred for 30 minutes under ice cooling. The reaction mixture was poured into ice water (1.5 L), and then ammonium chloride (300 g) was added to the reaction mixture with stirring. The target compound was extracted with ethyl acetate (1 L×2). The organic layer was washed sequentially with water (1 L) and saturated brine (1 L). The organic layer was dried over magnesium sulfate, and then the solvent of the organic layer was distilled off under reduced pressure. Thus, compound 9' (16.12 g, yield 66.0%) as a pale yellow brown solid was obtained.

Step 3

To a methylene chloride solution (500 mL) of compound 9' (17.07 g, 94.21 mmol) and p-toluenesulfonic acid monohydrate (18.11 g, 94.21 mmol), 3,4-dihydro-2H-pyrane (23.55 mL, 259.2 mmol) was added under ice cooling, and the reaction mixture was stirred for 18 hours at room temperature. The organic layer was washed sequentially with a saturated aqueous solution of sodium hydrogen carbonate (500 mL) and saturated brine (500 mL). The organic layer was dried over magnesium sulfate, and then the solvent of the organic layer was distilled off under reduced pressure. Thus, compound 10''' (42.72 g, crude yield 170.9%) as a pale yellow brown liquid was obtained. Compound 10''' was supplied to the subsequent step in a crude form.

Step 4

In an Ar atmosphere, a THF solution (200 mL) of crude compound 10''' (42.72 g, Net=24.99 g, 94.21 mmol) was added dropwise under ice cooling to a TI-IF suspension (100 mL) of lithium aluminum hydride (7.988 g, 210.5 mmol).

Thereafter, the reaction mixture was stirred for one hour at room temperature. Under ice cooling, water (8 mL), a 15% aqueous solution of sodium hydroxide (8 mL), and water (24 mL) were sequentially added dropwise to the reaction mixture to terminate the reaction. The obtained mixture was filtered, and the slurry was washed with ethyl acetate (600 mL). A obtained filtrate was washed with saturated brine (300 mL), and was dried over sodium sulfate. Subsequently, the solvent of the filtrate was distilled off under reduced pressure. The obtained residue was purified by medium pressure fractionation (silica gel 200 g, hexane/ethyl acetate=1/1 to ethyl acetate only), and thus compound 16' (14.98 g, yield from compound 9': 71.2%) as a pale yellow brown liquid was obtained.

Step 5

In an Ar atmosphere, sodium hydride (1489 g, 87.22 mmol in terms of 60%) was added in divided portions to a DMF solution (60 mL) of the compound 16' (14.98 g, 67.09 mmol) under ice cooling, and the reaction mixture was stirred for one hour at room temperature. Subsequently, compound 8 (10.53 g, 100.7 mmol) was added to the reaction mixture, and the mixture was stirred for 3 hours at 50° C. Ice water (300 mL) was added to the reaction mixture, and the target compound was extracted with ethyl acetate (300 mL). The organic layer was washed sequentially with water (300 mL) and saturated brine (300 mL). The organic layer was dried over magnesium sulfate, and then the solvent of the organic layer was distilled off under reduced pressure. The obtained residue was purified by medium pressure fractionation (silica gel 200 g, hexane/ethyl acetate=10/1 to 1/1), and compound 17' (15.40 g, yield 78.8%) as a pale yellow brown liquid was obtained.

Step 6

To a methanol solution (154 mL) of compound 17' (15.40 g, 52.85 mmol), p-toluenesulfonic acid monohydrate (502.7 mg, 2.643 mmol) was added, and the reaction mixture was stirred for 18 hours at room temperature. Thereafter, the reaction mixture was heated to reflux for 8 hours. The reaction mixture was concentrated, and the obtained residue was purified by medium pressure fractionation (silica gel 200 g, hexane/ethyl acetate=1/1 to ethyl acetate only). Thus, compound 18' (10.78 g, yield 98.4%) as a pale yellow brown liquid was obtained.

Step 7

In an Ar atmosphere, sodium hydride (2.430 g, 60.74 mmol in terms of 60%) was added in divided portions to a dioxane solution (100 mL) of compound 18' (10.76 g, 51.91 mmol) under ice cooling, and the reaction mixture was stirred for 15 minutes at room temperature. Subsequently, a dioxane solution (60 mL) of compound 5b (18.24 g, 60.74 mmol) was added thereto, and the reaction mixture was stirred for 2 hours at 50° C. Ice water (300 mL) was added to the reaction mixture, and the target compound was extracted with ethyl acetate (200 mL×2). The organic layer was washed with saturated brine (200 mL). The organic layer was dried over sodium sulfate, and then the solvent of the organic layer was distilled off under reduced pressure. The obtained residue was purified by medium pressure fractionation (silica gel 200 g, hexane/ethyl acetate=4/1 to ethyl acetate only), and thus compound 19 (14.21 g, yield 81.6%) as a pale yellow brown liquid was obtained.

Step 8

In an Ar atmosphere, potassium t-butoxide (49.00 g, 436.7 mmol) was added to a DMSO solution (375 mL) of compound 19 (14.21 g, 43.67 mmol), and the reaction mixture was stirred for 30 minutes at 60° C. The reaction mixture was poured into ice water (1 L), and the target compound was extracted with ethyl acetate (500 mL×4). The organic layer was washed with saturated brine (500 mL), and was dried over sodium sulfate. Thereafter, the solvent of the organic layer was distilled off under reduced pressure. The obtained residue was purified by medium pressure fractionation (silica gel 200 g, hexane/ethyl acetate=1/1 to ethyl acetate only), and thus compound 11" (4.201 g, yield 37.1%) as a pale yellow liquid was obtained.

Step 9

In an Ar atmosphere, a THF solution (23 mL) of diisopropyl azodicarboxylate (DIAD, 4.768 g, 23.58 mmol) was added dropwise to a THF solution (200 mL) of compound 4 (3.185 g, 15.72 mmol), compound 11" (4.201 g, 15.72 mmol) and triphenylphosphine (6.185 g, 23.58 mmol) under ice cooling, and the reaction mixture was stirred for 16 hours at room temperature. The reaction mixture was concentrated, and the obtained residue was purified by medium pressure fractionation (silica gel 200 g, hexane/ethyl acetate=4/1 to 1/1, two times), and thus compound 12" (431 mg, yield 6.1%) as a slight yellow liquid was obtained.

Step 10 p-Toluenesulfonic acid monohydrate (9.05 mg, 0.0457 mmol) was added to a methanol solution (4.3 mL) of compound 12" (430 mg, 0.9515 mmol), and the reaction mixture was stirred for 18 hours at room temperature. The reaction mixture was further stirred for 4 hours at 60° C. The reaction mixture was concentrated, and the obtained residue was purified by medium pressure fractionation (silica gel 60 g, hexane/ethyl acetate=3/1 to ethyl acetate only), and compound 13" (242 mg, yield 69.2%) as a colorless liquid was obtained. The NMR spectrum of compound 13" is shown in FIG. 1.

Step 11

To a methylene chloride solution (3 mL) of compound 13" (140.6 mg, 0.3822 mmol), triethylamine (386.7 mg, 3.822 mmol) and 4-dimethylaminopyridine (4.67 mg, 0.03822 mmol), p-toluenesulfonyl chloride (109.3 mg, 0.5734 mmol) was added at −10° C. After p-toluenesulfonyl chloride was added, the reaction mixture was stirred for 16 hours at −10° C. Ice water (20 mL) was poured into the reaction mixture, and the target compound was extracted with methylene chloride (20 mL). The organic layer was washed with saturated brine (10 mL), and was dried over magnesium sulfate. Thereafter, the solvent of the organic layer was distilled off under reduced pressure, and compound 14" (201.2 mg, crude yield 100.8%) that was a red brown viscous liquid, was obtained. Compound 14" was immediately supplied to the subsequent step, while being in a crude form.

Step 12

Crude compound 14" (195 mg, Net=193.5 mg, 0.3706 mmol) was dissolved in THF (2 mL), and 1 M TBAF/THF (2 mL) and TBAF.xH$_2$O (500 mg) were added thereto. The reaction mixture was stirred for 2 hours at room temperature. Ice water (50 mL) was poured into the reaction mixture, and the target compound was extracted with ethyl acetate (50 mL). The organic layer was washed with saturated brine (20 mL), and was dried over magnesium sulfate. Thereafter, the solvent of the organic layer was distilled off under reduced pressure. The obtained residue was purified by medium pressure fractionation (silica gel 60 g, hexane/ethyl acetate=4/1 to 1/1), and together with a lot separately produced and purified from compound 13" (50 mg), compound 15" (BMS-P) (47.6 mg, yield 25.4%) as a red brown liquid was obtained.

Evaluation of Binding Affinity to Mitochondrial Complex-1

Dose-response curves of a test substance and a positive substance were produced, and the concentrations at which the test substance and the positive substance suppress 50% of the binding between a tracer and mitochondrial Complex-1 (receptor) ($IC_{50}$ value), and the absolute inhibition constant (Ki) were calculated. For the test substance, BMS, BCPP-EF, BCPP-BF, BCPP-PF, BCPP-EM, and BMS-P were used. The details are described below.

Preparation of Undiluted Solution of Mitochondrial Fraction

An animal tissue was weighed (wet weight), a twice amount of a homogenate buffer solution (10 mmol/L Tris-HCl buffer solution (pH 7.40) of 250 mmol/L sucrose, 1 mmol/L succinic acid, and 0.2 mmol/L EDTA) was added thereto, and the mixture was homogenized under ice cooling. Thereafter, the homogenized suspension was centrifuged (1200×g, 4° C., for 20 minutes), and the supernatant was collected and centrifuged (26000×g, 4° C., for 15 minutes). A precipitated residue was collected, a homogenate buffer solution was added thereto so as to obtain a concentration of 100 mg tissue eq./mL, and the mixture was homogenized. The obtained undiluted solution of the mitochondrial fraction was stored at −80° C. until use. The protein concentration of the undiluted solution of the mitochondrial fraction was measured using BCA Protein Assay Reagent (manufactured by Pierce Biotechnology, Inc.). For the animal tissue, rat brain and bovine heart were used.

Preparation of Mitochondrial Fraction Solution

A mitochondrial fraction solution having a concentration of twice the final concentration was prepared by diluting the undiluted solution of mitochondrial fraction with a buffer solution (preparation upon use). The final concentration of the mitochondrial fraction solution was adjusted to 45 μg protein/mL.

Preparation of Test Substance Solution

A test substance was diluted stepwise with DMSO, and thereby a solution at a concentration 100 times the final concentration was produced. Furthermore, the solutions thus produced at various concentrations were diluted 10 times with Milli-Q water, and thereby test substance solutions at a concentration 10 times the final concentration were prepared (preparation upon use).

The final concentrations of the test substances were set to the following concentration ranges:

BMS; $3\times10^{-11}$ to $3\times10^{-8}$ mol/L
BCPP-EF; $1\times10^{-10}$ to $1\times10^{-7}$ mol/L
BCPP-BF; $3\times10^{-11}$ to $3\times10^{-8}$ mol/L
BCPP-PF; $1\times10^{-10}$ to $1\times10^{-7}$ mol/L
BCPP-EM; $3\times10^{-10}$ to $3\times10^{-7}$ mol/L.

Preparation of Positive Substance Solution

A positive substance was weighed and dissolved in DMSO. The obtained solution was diluted stepwise with DMSO, and thereby a solution at a concentration 100 times the final concentration was prepared. Furthermore, the prepared solutions at various concentrations were diluted 10 times with Milli-Q water, and thereby positive substance solutions at a concentration 10 times the final concentration were prepared (preparation upon use). Rotenone was used as the positive substance. The final concentration of the positive substance was adjusted to $3\times10^{-11}$ to $3\times10^{-8}$ mol/L.

Preparation of Substituent Substance Solution

A substituent substance was weighed and dissolved in DMSO, and thereby a solution at a concentration 100 times the final concentration was prepared. Furthermore, the prepared solution was diluted 10 times with Milli-Q water, and thereby a substituent substance solution at a concentration 10 times the final concentration was prepared (preparation upon use). Rotenone was used as the substituent substance. The final concentration of the substituent substance was adjusted to $1\times10^{-5}$ mol/L.

Preparation of Tracer Solution

A tracer solution at a concentration of 10 times the final concentration was prepared by diluting an undiluted tracer solution with a buffer solution (preparation upon use). Dihydrorotenone[2-isopropyl-$^3$H(N)] was used as the tracer. The final concentration of the tracer was 4.5 nmol/L for the first time, 4.4 nmol/L for the second time, and 4.5 nmol/L for the third time.

Measurement Procedure

A measurement was carried out according to the following procedure. Two exemplary samples were prepared for each of various concentrations, and measurements were made three times respectively.

1: In a tube for calculating non-specific binding, 100 μL of the substituent substance solution was introduced (final concentration of DMSO: 1%). In a tube for calculating the total binding, 100 μL of 10% DMSO was introduced (final concentration of DMSO: 1%). In a tube for calculating the inhibition ratio of the test substance or the positive substance, 100 μL each of a test substance solution or a positive substance solution was introduced (final concentration of DMSO: 1%).

2: A buffer solution (300 μL) was introduced into each of the tubes.

3: The tracer solution (100 μL) was introduced into each of the tubes.

4: The mitochondrial fraction solution (500 μL) was introduced into each of the tubes.

5: The reaction mixtures included in the various tubes were incubated for 30 minutes at 22° C.

6: The reaction mixture was filtered (GF/C, Whatman) using a cell harvester, and the filtered filter paper was washed three times with 50 mmol/L of a Tris-HCl buffer solution (pH 7.40, 3 mL).

7: The filter paper was transferred to a vial bottle for measurement, a liquid scintillator (PICO-FLUOR™ PLUS, 5 mL) was added thereto, and the amount of radioactivity was measured (measurement time: 2 minutes) with a liquid scintillation counter.

Calculation of Inhibition Ratio

The inhibition ratio was calculated by the formula of "100-binding ratio".

$$\text{Binding ratio: } [(B-N)/(B_0-N)]\times 100(\%)$$

B: Amount of bound radioactivity in the presence of a test substance (individual value)

$B_0$: Amount of total bound radioactivity in the absence of a test substance (average value)

N: Amount of non-specific bound radioactivity (average value)

The inhibition ratio was calculated as 0% when the inhibition ratio was 0% or less, and the inhibition ratio was calculated as 100% when the inhibition ratio was more than 100%.

Also for the positive substance, the inhibition ratio was calculated in the same manner as in the case of the test substance.

Production of Dose-Response Curve (Calculation of $IC_{50}$ Value)

A dose-response curve was produced by subjecting the ratio of specific bound radioactivity (B−N) in the presence of a test substance and the total bound radioactivity ($B_0$−N)

in the absence of a test substance (($B-N$)/($B_0-N$)) to logit conversion, and then applying the resultant to a logit-log model of plotting the ratio against the common logarithm value of the final concentration of the test substance.

Regression of the dose-response curve was carried out using the following regression formula.

$Y=aX+b$ (Y=logit y=ln(y/(1−y)), y=($B-N$)/($B_0-N$))
(X=log x, x represents the final concentration of the test substance)
(a=integer, b=integer)

The $IC_{50}$ value was calculated from the obtained regression formula. At the time of performing regression, an inhibition ratio average exceeding the range of 5% to 95% at the final concentration of the test substance was not employed, and the $IC_{50}$ value was calculated by using an inhibition ratio that continuously increased within the range.

Calculation of Ki Value

The Ki values of a test substance and a positive substance were calculated by the following formula, using the tracer concentration (L) used in the test for calculating the $IC_{50}$ value, the obtained $IC_{50}$ value, and the Kd value of the tracer against the mitochondrial Complex-1 determined by a test based on Scatchard analysis.

$$Ki = \frac{IC_{50}}{1+\frac{L}{Kd}} \quad [\text{Math. 1}]$$

Figure 2:
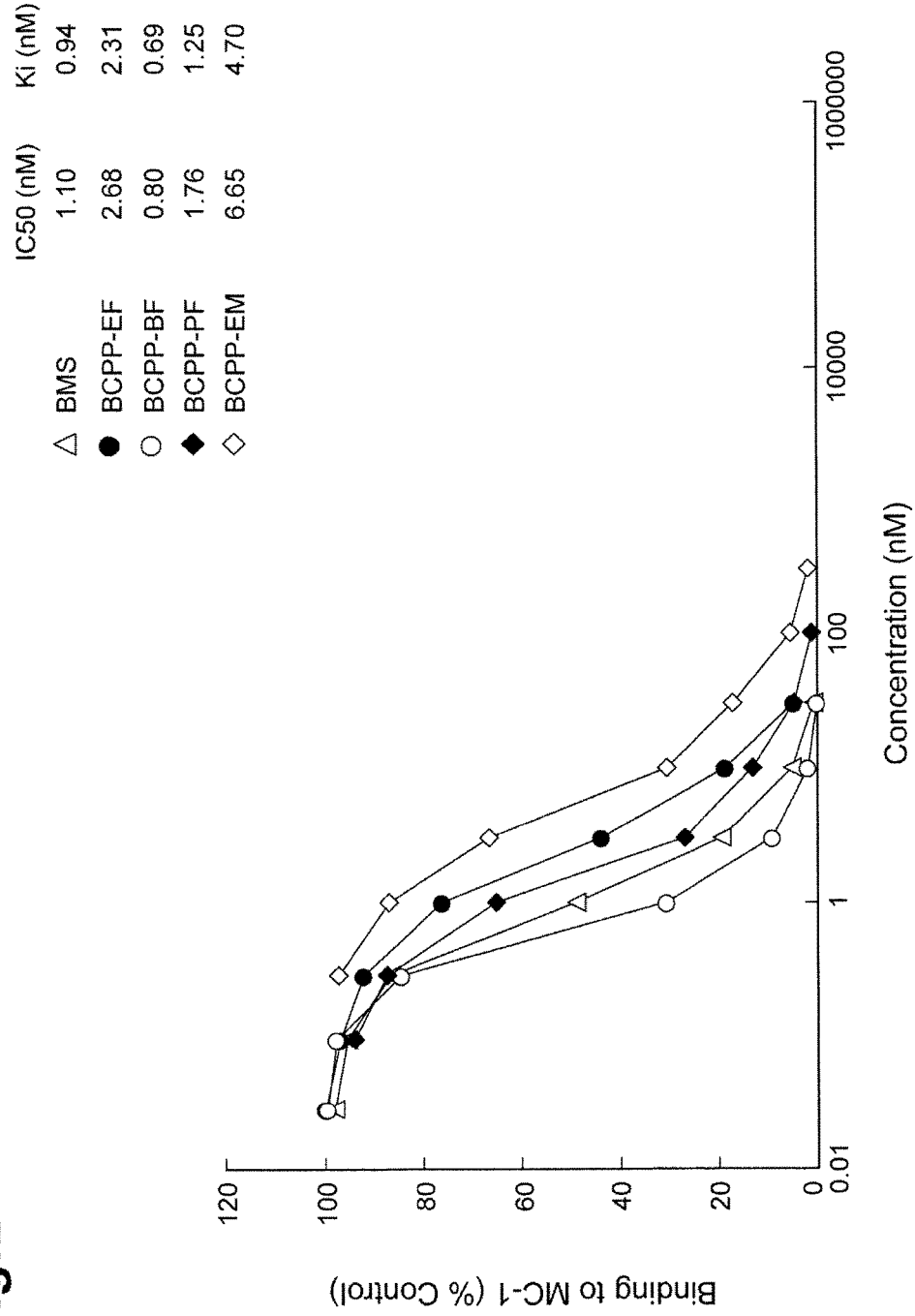
FIG. 2 is a graph showing the binding affinity to mitochondrial Complex-1.

A dose-response curve is shown in FIG. 2. It was found that all of the substances bind to mitochondrial Complex-1 in a concentration dependent manner. BCPP-BF exhibited the lowest $IC_{50}$, and thus it was suggested that BCPP-BF has high affinity to mitochondrial Complex-1.

Evaluation Using Living Slices of Rat

Figure 3:
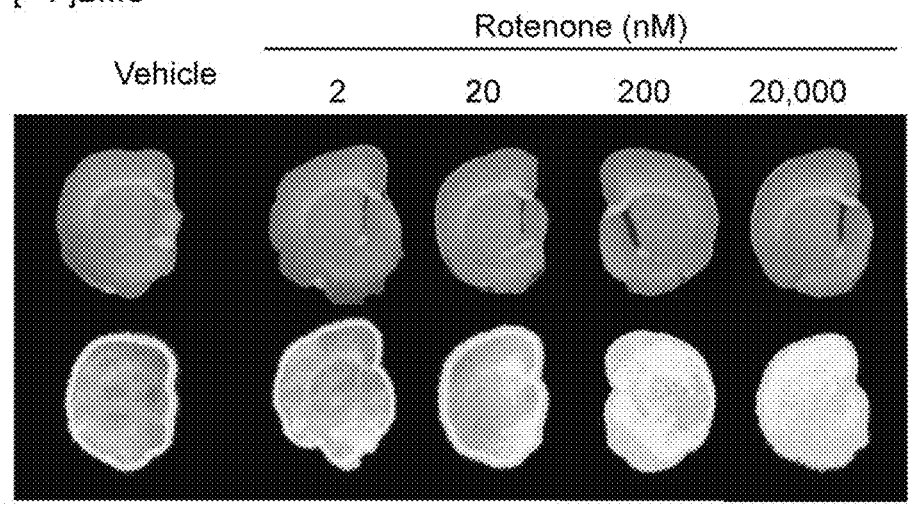
FIG. 3 is a diagram of images showing the effect on the inhibition of binding of a PET probe provided by inhibitory drugs that are specific to mitochondrial Complex-1 in a rat brain slice.
Figure 3:
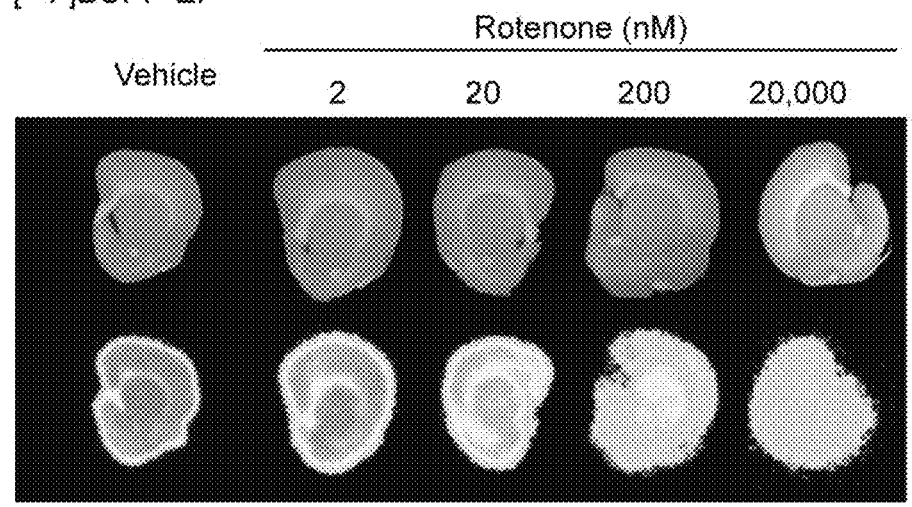
Figure 4:
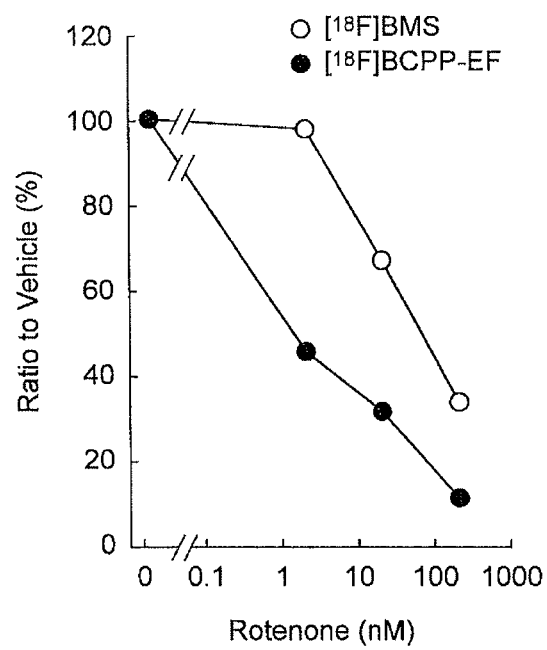
FIG. 4 is a graph showing the effect on the inhibition of binding of a PET probe provided by inhibitory drugs that are specific to mitochondrial Complex-1 in a rat brain slice.

A rat was anesthetized with chloral hydrate (400 mg/kg; I.P.) and decapitated. Thereafter, the brain was immediately sampled and cooled sufficiently, and the cooled brain was immersed in ACSF (artificial cerebrospinal fluid) in a sherbet state. A necessary block of the obtained brain was cut and adhered to a fixing platform of a vibration microtome HM650V (Thermo Fisher Scientific, Inc., Waltham, USA). Thereafter, brain slices having a thickness of 300 μm were produced. The cut brain slices were immersed in 24 ml of ACSF for 30 minutes under bubbling with $O_2$, and thus the activities of cells were calmed. Thereafter, 20 μL of Vehicle or Rotenone (adjusted to concentrations of 2 nM, 20 nM, 200 nM, and 20000 nM in respective beakers) was added to ACSF, and the mixture was bubbled for 30 minutes. Furthermore, 1 MBq/ml of [$^{18}$F]BMS or [$^{18}$F]BCPP-EF was added to the ACSF, and bubbling was continued for 30 minutes. After completion of the bubbling, the brain slices were taken out and transferred to 100 ml of fresh ACSF. Subsequently, excess RI was washed away by bubbling the ACSF for another 30 minutes. Thereafter, the brain slices were arranged in a row on an OHP sheet, and an image thereof was captured with a scanner (Epson: GT-600). Subsequently, the OHP sheet having the brain slices arranged in a row thereon was placed on an imaging plate (ST-VI, Fujifilm Corp., Tokyo) having sensitivity to radiation, and the OHP sheet was left to stand for about one hour in the dark (contact). The imaging plate was subjected to detection with a Fluoro Image Analyzer, FLA-7000 (Fujifilm Corp., Tokyo). The results are presented in FIGS. 3 and 4. It was found that [$^{18}$F]BCPP-EF is more likely to be affected by the binding inhibitory effect by rotenone than [$^{18}$F]BMS. This suggests that [$^{18}$F]BCPP-EF has higher specificity to mitochondrial Complex-1 than [$^{18}$F]BMS. The same experiment was also carried out for [$^{18}$F]BCPP-BF, [$^{18}$F]BCPP-PF and [$^{18}$F]BCPP-EM, and it was confirmed that these compounds are affected by the binding inhibitory effect of rotenone.

PET Analysis of Rotenone-Administered Rat

Figure 5:
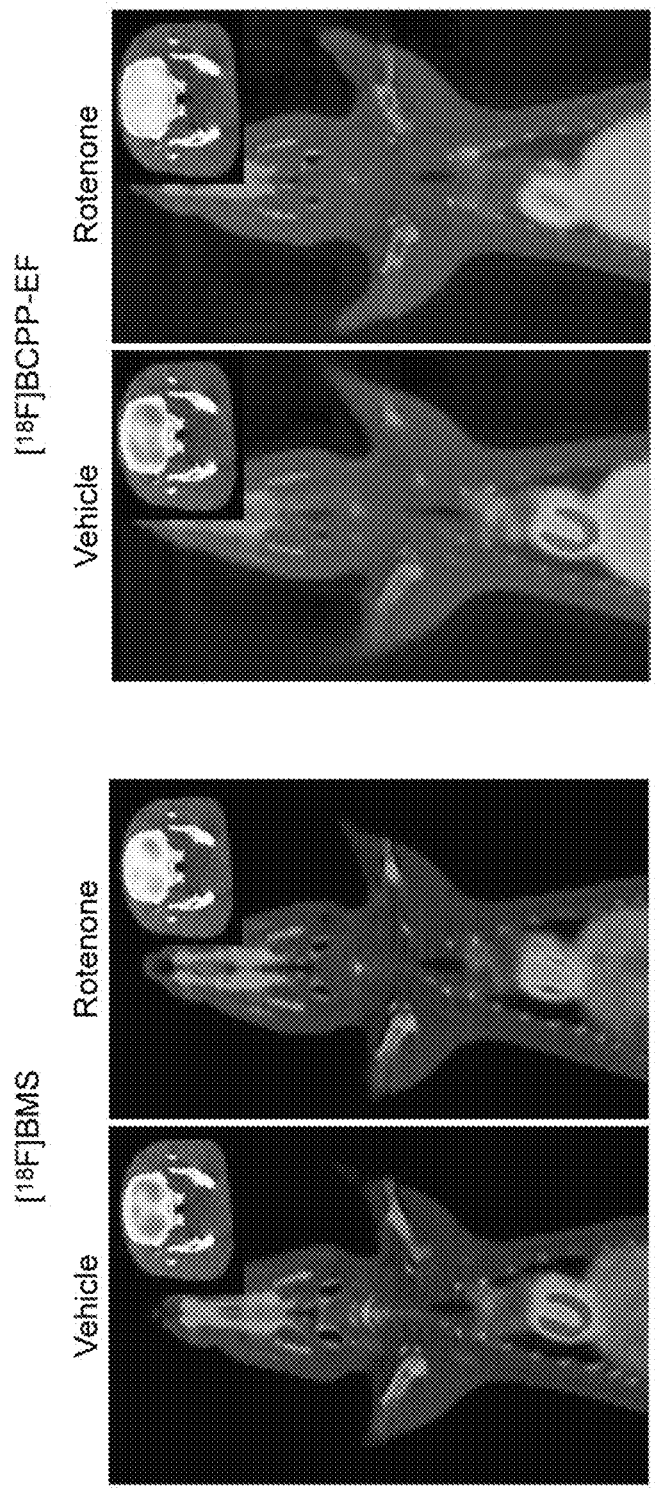
FIG. 5 is a diagram of PET images showing the effect on the inhibition of binding of a PET probe provided by inhibitory drugs that are specific to mitochondrial Complex-1 in the brain and heart of a living rat.
Figure 6:
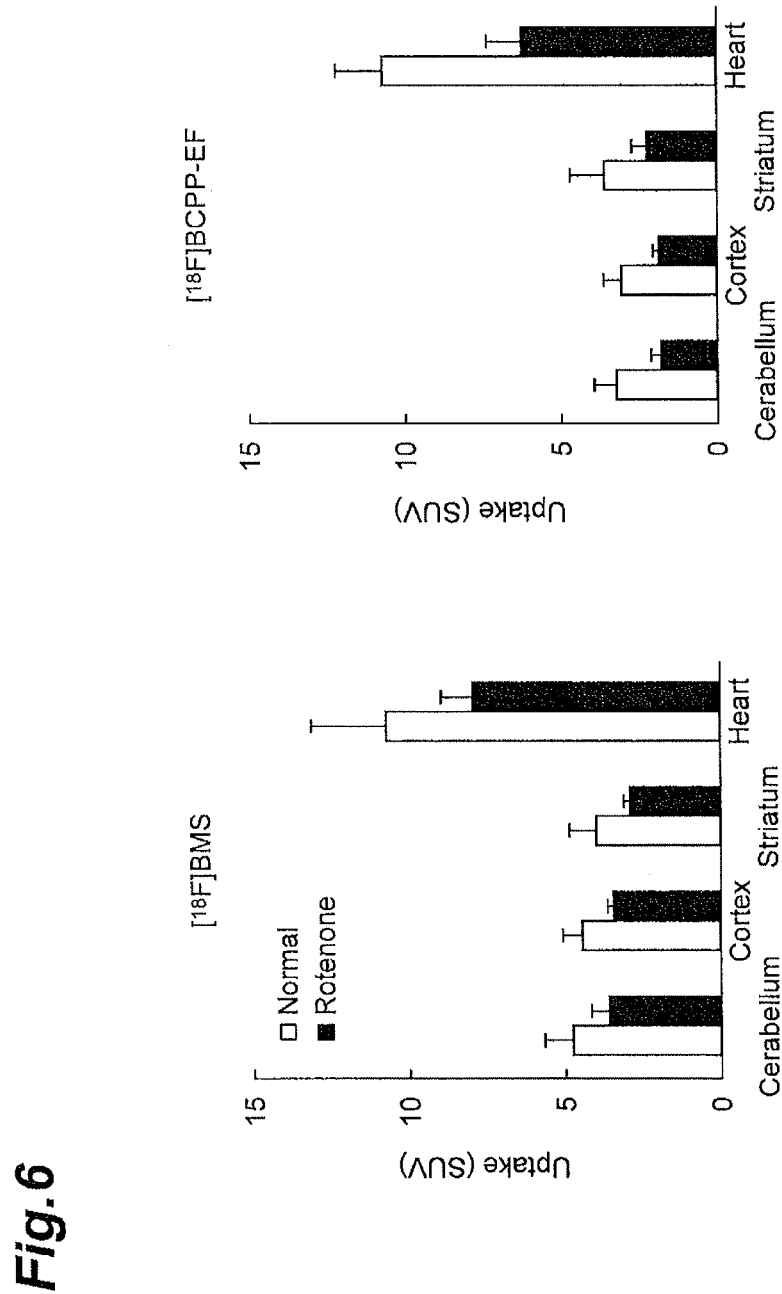
FIG. 6 is graphs showing the effect on the inhibition of binding of a PET probe provided by inhibitory drugs that are specific to mitochondrial Complex-1 in the brain and heart of a living rat.

A rat was anesthetized with chloral hydrate (400 mg/kg; I.P.) and was immobilized on a bed for measurement. Immediately thereafter, rotenone (0.1 mg/kg/h) or a vehicle was administered through the tail vein of the rat. In order to identify the position of the brain during the administration, an analysis was carried out using Clairvivo-CT (Shimadzu Corp.). Thereafter, the bed for measurement was moved to Clairvivo PET. After the administration of rotenone (0.1 mg/kg/h) or the vehicle was completed, [$^{18}$F]BMS or [$^{18}$F]BCPP-EF was immediately bolus administered in an amount of about 8 MBq/animal through the tail vein of the rat, and the measurement was carried out for 60 minutes. During the measurement, chloral hydrate (100 mg/kg/hr) was continuously administered through the tail vein of the rat, and thereby the rat was inactivated. The binding inhibitory effect induced by rotenone was observed for the cerebellum, cerebral cortex, corpus striatum, and heart of the rat. The results are presented in FIGS. 5 and 6. It was found that in all of the tissues, the uptake quantity of [$^{18}$F]BCPP-EF was further reduced by the administration of rotenone than that of [$^{18}$F]BMS.

Production of Rat Cerebral Infarction Model with Blocked Middle Cerebral Artery and PET Analysis An experiment was carried out using a cerebral infarction (photochemically induced thrombosis: PIT) model of a rat in which the middle cerebral artery (MCA) was actually blocked with thrombi, similarly to the case of a human, by utilizing a photosensitization reaction. The rat was subjected to anesthesia induction using 4% halothane (30% $O_2$, 70% room air), and during the surgery, the halothane concentration was maintained at 1.5% to 2%. The skin was incised along the left eye cavity margin under a surgical microscope, and an elliptical window (hole) having a size of about 3 mm was cut open in the lower cranium using a dental drill so that the left middle cerebral artery could be seen under the dura mater. Photosensitizer Rose Bengal (20 mg/kg) was administered through the tail vein of the rat, the middle cerebral artery was irradiated with green light having a wavelength of 540 nm for 10 minutes, and thus cerebral infarction was developed in the rat.

Figure 7:
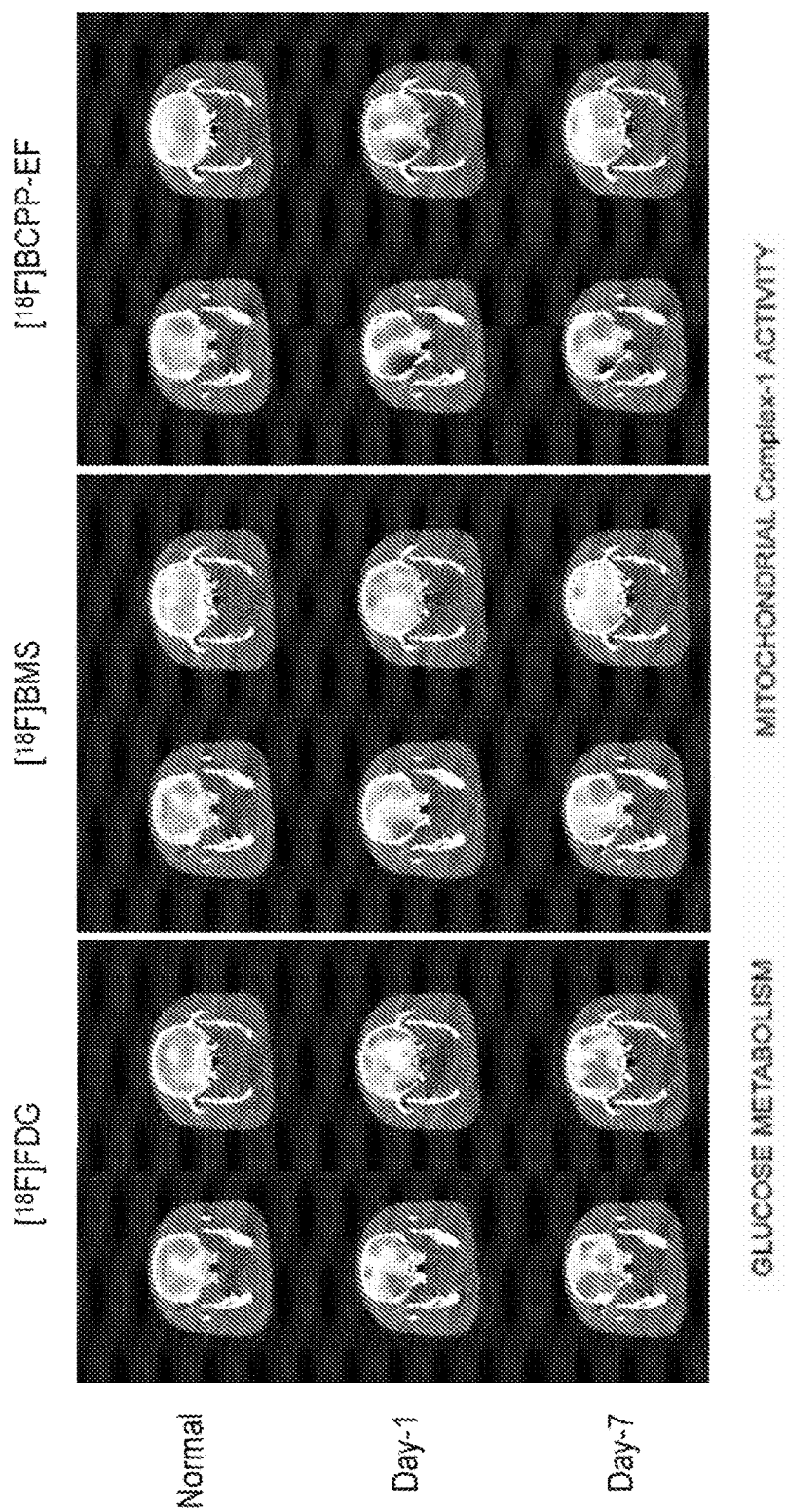
FIG. 7 is a diagram of PET images showing changes over time in the glucose metabolism and in the activity of mitochondrial Complex-1 in a site of injury of a rat cerebral infarction model.

In the respective rats before the onset of cerebral infarction (Normal), 1 day after the onset of cerebral infarction (Day-1), and 7 days after the onset of cerebral infarction (Day-7), glucose metabolism (using [$^{18}$F]FDG as a probe) and the activity of mitochondrial Complex-1 (using [$^{18}$F]BMS or [$^{18}$F]BCPP-EF as a probe) in the sites of ischemic disorder in the brain were monitored by the PET method. Specifically, each of the probes was bolus administered in an amount of 6 to 8 MBq/animal through the tail vein of the rat, and the analysis was carried out for 60 minutes. During the analysis, the rat was inactivated by continuously administering chloral hydrate (100 mg/kg/hr) through the tail vein of the rat. The results are presented in FIG. 7. It was found that when [$^{18}$F]FDG was used as the probe, accumulation of [$^{18}$F]FDG increased in the site of ischemic disorder. This suggests that [$^{18}$F]FDG is not suitable as a PET probe for an evaluation after a neurological disorder. On the other hand, it could been seen that when [$^{18}$F]BMS or [$^{18}$F]BCPP-EF was used as the probe, no accumulation of the probe was observed in the site of ischemic disorder, and the activity of mitochondrial Complex-1 could be accurately evaluated. Particularly when [$^{18}$F]BCPP-EF was used as the probe, it was found that the degree of accumulation of the probe was clearly different between a site of ischemic disorder and a normal site, as compared with [$^{18}$F]BMS. This shows that [$^{18}$F]BCPP-EF is suitable as a probe for evaluating the intracerebral functions.

PET Analysis Using Monkey

An experiment for inhibiting the binding of a PET probe by rotenone administration in the brain of a monkey, variation in the intracerebral activity of mitochondrial Complex-1 brought by aging, and an evaluation of the intracerebral activity of mitochondrial Complex-1 in a Parkinson's disease model monkey were carried out. For all of the experiments, the PET analysis was carried out by the following method.

Cephalic vein or saphenous vein was secured as the route of intravenous administration to the test animal, and femoral artery or posterior tibial artery was secured as the route for collecting arterial blood. First, the amount of radioactivity of [$^{18}$F]BMS, [$^{18}$F]BCPP-EF or [$^{11}$C]BCPP-EM was measured. As radioactive agents, [$^{18}$F]BMS and [$^{18}$F]BCPP-EF were administered through an indwelling needle indwelled in a test animal in an amount of administration of 300 to 500 MBq, and [$^{11}$C]BCPP-EM was administered in an amount of administration of 800 to 1200 MBq, such that the entire amount of the radioactive agent was intravenously administered over about 30 seconds. Simultaneously with the initiation of administration of the radioactive agent, measurement of emission (6 frames of 10 seconds, 6 frames of 30 seconds, 12 frames of 1 minute, 25 frames of 3 minutes, and 6 frames of 5 minutes; 55 frames for 121 minutes in total) was initiated.

Figure 8:
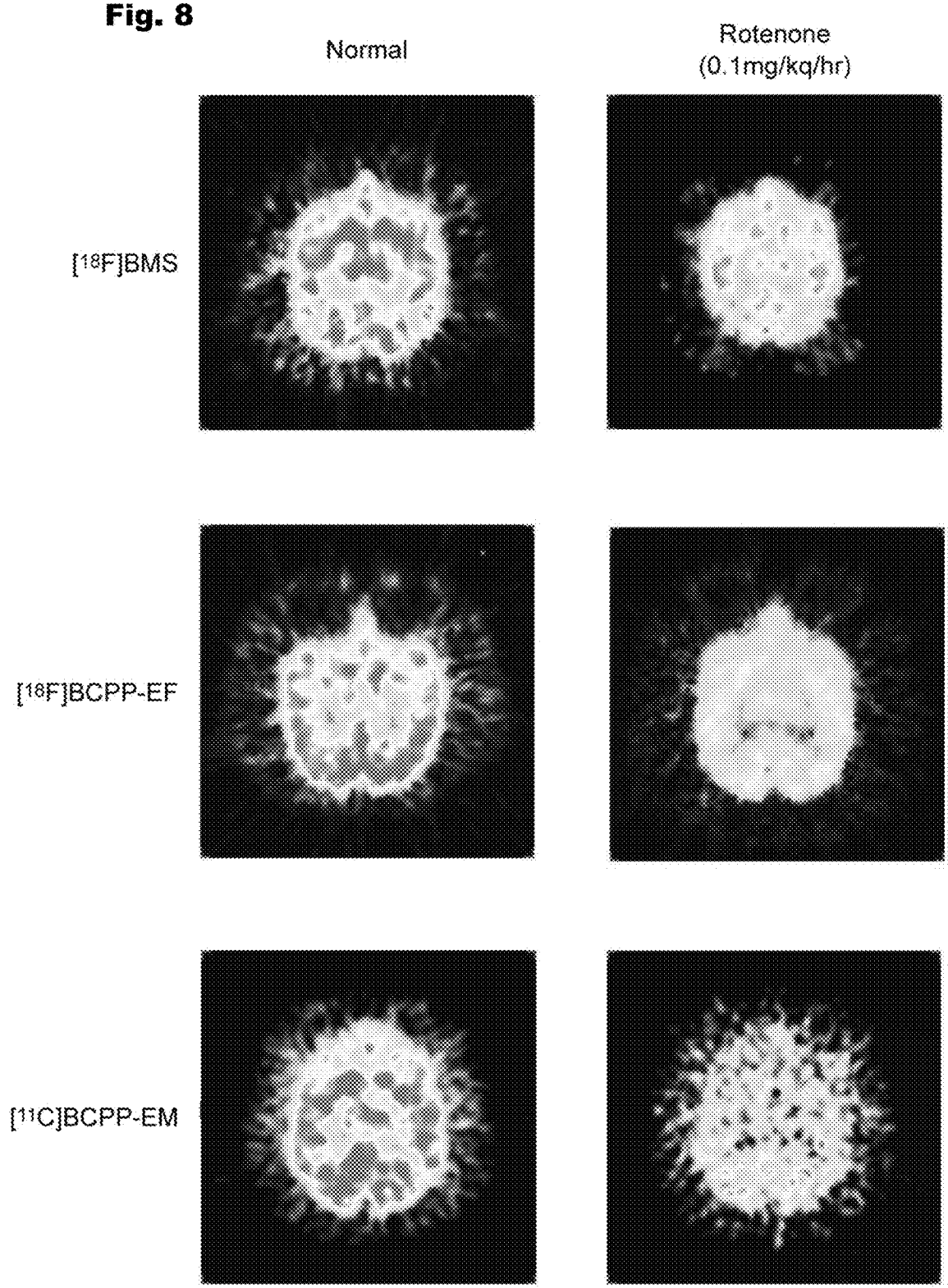
FIG. 8 is a diagram of PET images showing the effect on the inhibition of binding of a PET probe provided by inhibitory drugs that are specific to mitochondrial Complex-1 in the brain of a living monkey.
Figure 9:
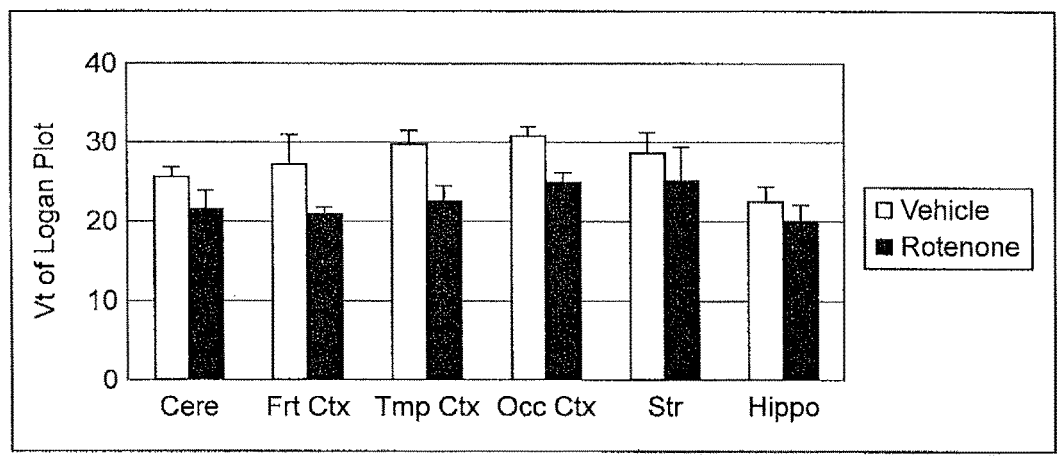
FIG. 9 is graphs showing the effect on the inhibition of binding of a PET probe provided by inhibitory drugs that are specific to mitochondrial Complex-1 in the brain of a living monkey.
Figure 9:
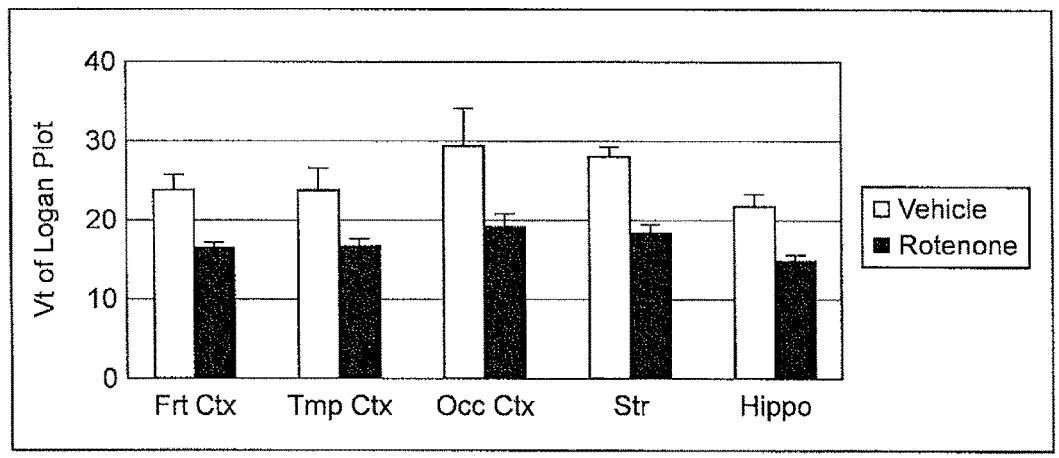

Experiment on Inhibition of Binding to Mitochondrial Complex-1 by Rotenone Administration In the experiment on the inhibition of PET probe binding by rotenone administration in the brain of a monkey, rotenone was administered to the test animal by intravenous injection in an amount of 0.1 mg/kg/hr. Subsequently, [$^{18}$F]BMS, [$^{18}$F]BCPP-EF or [$^{11}$C]BCPP-EM was administered as a probe, and a PET analysis was carried out. The results are presented in FIGS. 8 and 9. It was found that [$^{18}$F]BCPP-EF and [$^{11}$C]BCPP-EM were more likely to be affected by the binding inhibitory effect of rotenone, as compared with [$^{18}$F]BMS. It was also found that in the case of monkey, [$^{18}$F]BCPP-EF and [$^{11}$C]BCPP-EM have higher specificity to mitochondrial Complex-1 than [$^{18}$F]BMS.

Variation of Intracerebral Activity of Mitochondrial Complex-1 Brought by Aging

Figure 10:
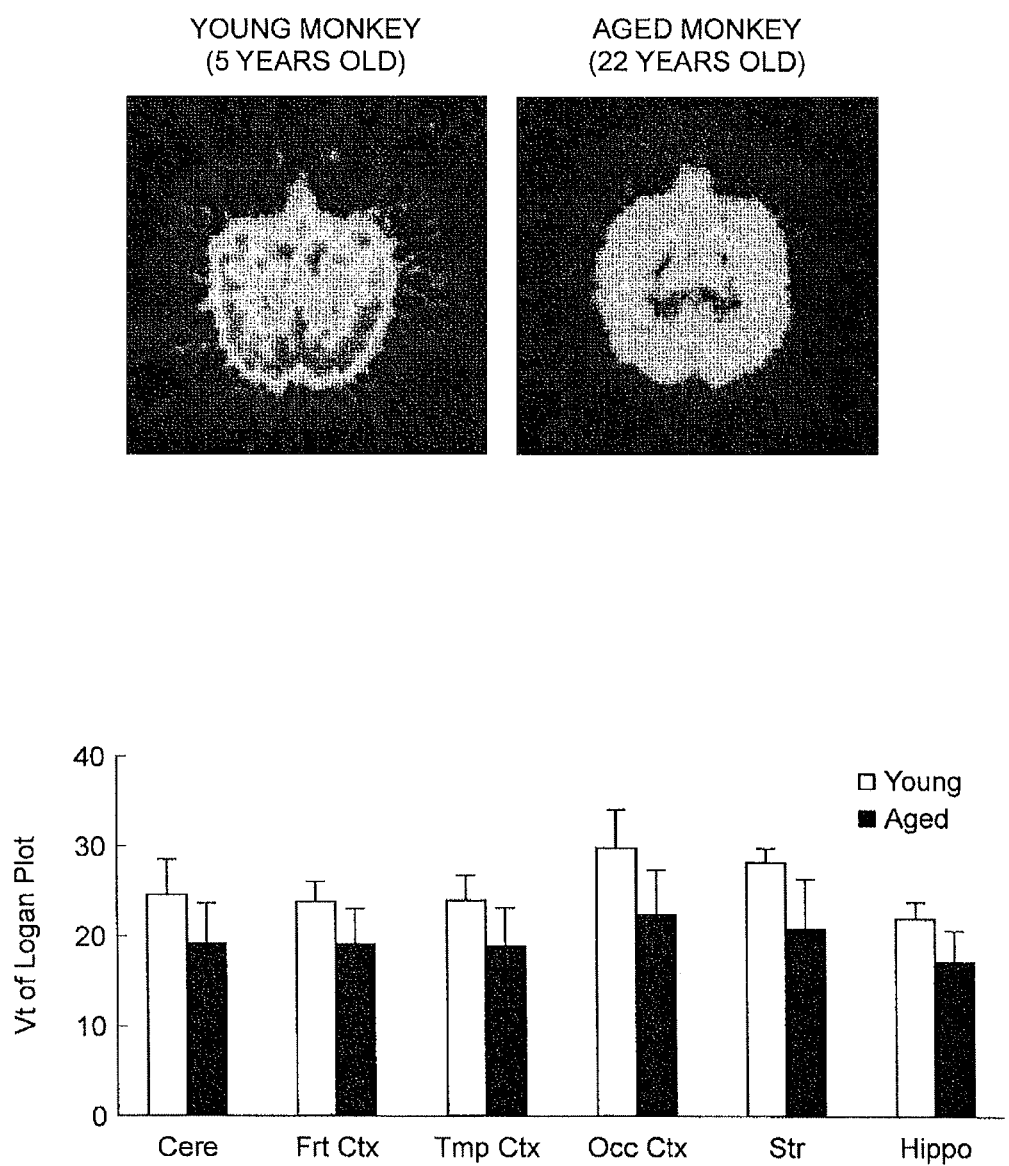
FIG. 10 is a diagram of PET images and a graph showing the correlation between the binding of [$^{18}$F]BCPP-EF and aging in the brain of a living monkey.

The results of a PET analysis obtained from a young monkey (5 years old) and an aged monkey (22 years old) are presented in FIG. 10. [$^{18}$F]BCPP-EF was used as the PET probe. It was found that a larger amount of the PET probe was accumulated in the brain in the young monkey than in the aged monkey. This suggests that the intracerebral activity of mitochondrial Complex-1 has been decreased by aging.

Figure 11:
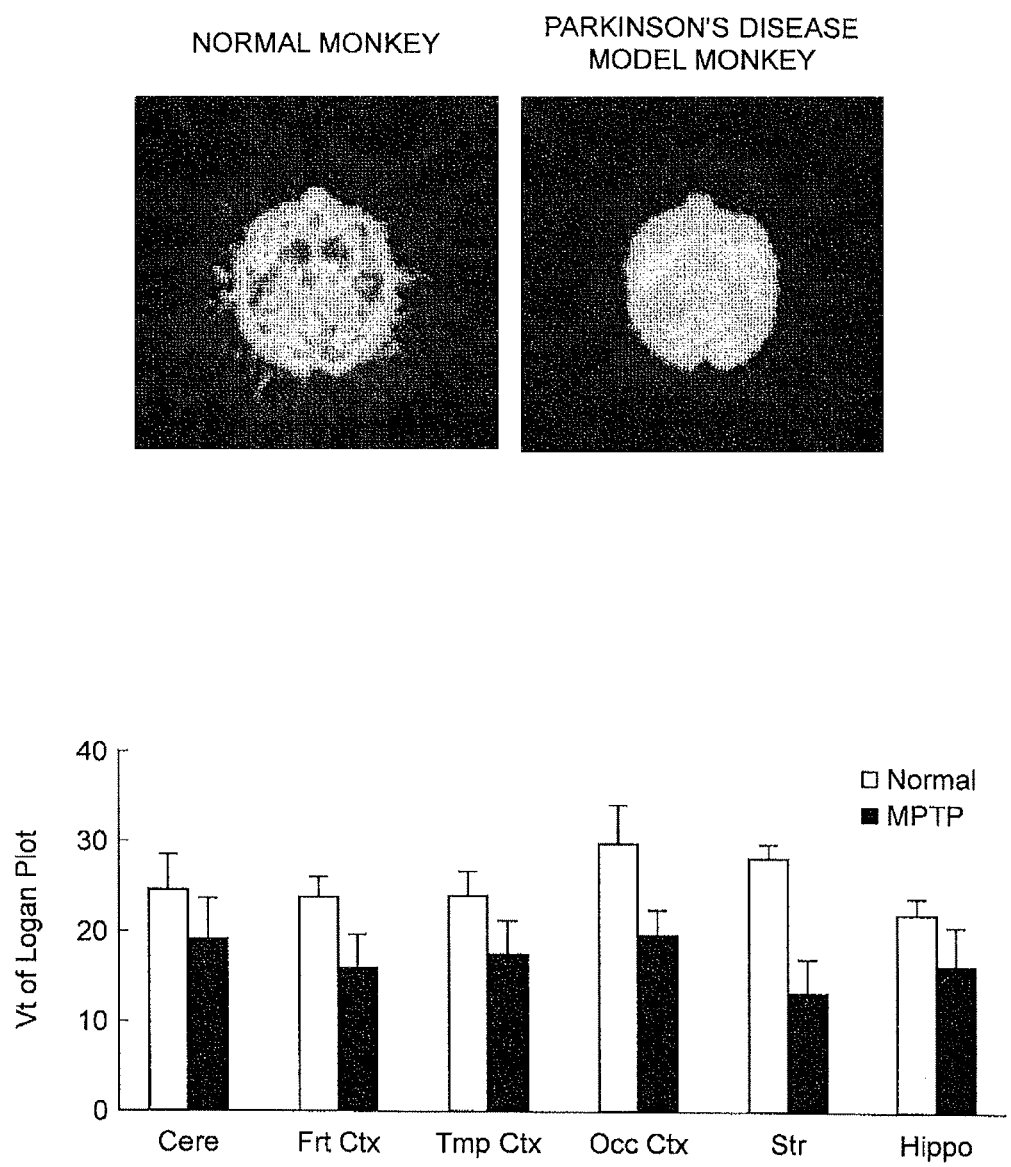
FIG. 11 is a diagram of PET images and a graph showing the binding of [$^{18}$F]BCPP-EF in the brains of a normal monkey and a Parkinson's disease model monkey.

Evaluation of Intracerebral Activity of Mitochondrial Complex-1 in Parkinson's Disease Model Monkey A comparison of the intracerebral activity of mitochondrial Complex-1 was made between a normal monkey and a Parkinson's disease model monkey by a PET analysis. [$^{18}$F]BCPP-EF was used as the PET probe. A Parkinson's disease model monkey was prepared as follows. MPTP (1-methyl-4-phenyl-1,2,3,6-tetrahydropyridine) that selectively impairs dopaminergic neurons was administered to a young male *Macaca fascicularis* monkey (body weight 3 to 6 kg), in an amount of 15 to 20 mg as a total amount of MPTP over 6 months at a rate of once a week. The administration of MPTP was conducted while checking the health condition of the *Macaca fascicularis* monkey. The degree of motility disturbance in the limbs was evaluated by observing the way that the *Macaca fascicularis* monkey picked up the feed, and also, by measuring the decrease in the sites of dopamine reabsorption using a PET analysis, it was finally confirmed that the *Macaca fascicularis* monkey had the condition of Parkinson's disease. The results are presented in FIG. 11. It was found that the amount of the PET probe accumulating in the brain was smaller in the Parkinson's disease model monkey, compared with the normal monkey. This suggests that there is a correlation between the onset of Parkinson's disease and the activity of mitochondrial Complex-1.

The invention claimed is:

1. A compound represented by formula (1-0'):

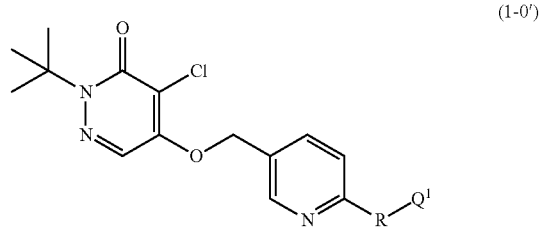

(1-0')

wherein in formula (1-0'), R represents —O(CH$_2$)$_2$OC$_2$H$_4$—; and Q$^1$ represents F or —OCH$_3$.

2. A compound represented by formula (1-0'):

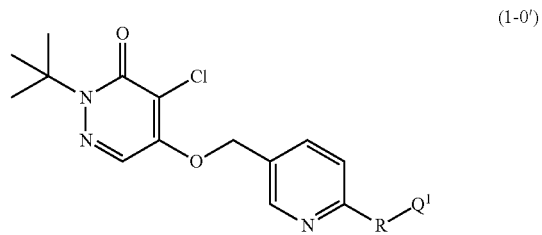

(1-0')

wherein in formula (1-0'), R represents —O(CH$_2$)$_2$OC$_2$H$_4$—; and Q$^1$ represents $^{18}$F or —O$^{11}$CH$_3$.

3. A compound represented by formula (2-0'):

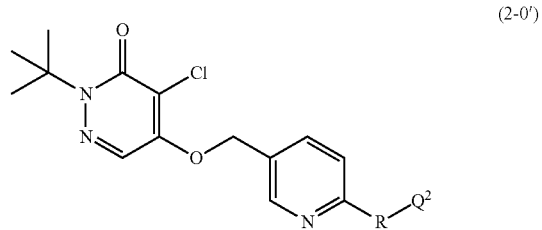

(2-0')

wherein in formula (2-0'), R represents —O(CH$_2$)$_2$OC$_2$H$_4$; and Q$^2$ represents a halogen atom, a hydroxyl group, or a substituted sulfonyloxy group selected from the group consisting of a tosyloxy group (—OTs), a methanesulfonyloxy group (—OMs), a trifluoromethanesulfonyloxy group (—OTf), and a nitrobenzenesulfonyloxy group (—ONs).

* * * * *